United States Patent
Du et al.

(10) Patent No.: US 7,169,564 B1
(45) Date of Patent: Jan. 30, 2007

(54) FKBP51/52 AND CYP40-MEDIATED MAMMALIAN HAIR GROWTH

(75) Inventors: Daniel Du, New Hyde Park, NY (US); John Douglas Haley, Sea Cliff, NY (US)

(73) Assignee: Anaderm Research Corporation, New York, NY (US)

( * ) Notice: Subject to any disclaimer, the term of this patent is extended or adjusted under 35 U.S.C. 154(b) by 603 days.

(21) Appl. No.: 10/178,832

(22) Filed: Jun. 24, 2002

Related U.S. Application Data

(60) Provisional application No. 60/300,876, filed on Jun. 26, 2001.

(51) Int. Cl.
*C12Q 1/02* (2006.01)
*G01N 33/566* (2006.01)

(52) U.S. Cl. .................. 435/7.1; 424/9.2; 435/7.2; 435/7.21; 435/7.24; 435/7.4; 435/29; 436/501

(58) Field of Classification Search ................ 435/7.1, 435/7.2, 7.21, 7.24, 7.4, 29; 436/501; 424/9.2
See application file for complete search history.

(56) References Cited

U.S. PATENT DOCUMENTS

| | | | | |
|---|---|---|---|---|
| 5,763,590 | A | 6/1998 | Peattie et al. | 536/23.5 |
| 5,837,251 | A | 11/1998 | Srivastava | 424/193.1 |
| 5,945,441 | A * | 8/1999 | Steiner et al. | 514/427 |
| 5,968,921 | A * | 10/1999 | Gold | 514/183 |
| 6,187,312 | B1 | 2/2001 | Srivastava | 424/193.1 |
| 6,984,495 | B2 * | 1/2006 | Thompson | 435/7.1 |
| 2004/0086945 | A1 * | 5/2004 | Sreekrishna et al. | 435/7.1 |

FOREIGN PATENT DOCUMENTS

| | | |
|---|---|---|
| JP | 11-174041 | 7/1999 |
| WO | WO 98/55090 | 12/1998 |
| WO | WO 99/38965 | 8/1999 |
| WO | WO00/72810 | 3/2000 |
| WO | WO00/72811 | 3/2000 |
| WO | WO00/72812 | 3/2000 |
| WO | WO00/72813 | 3/2000 |
| WO | WO00/72920 | 3/2000 |
| WO | WO00/73292 | 3/2000 |

OTHER PUBLICATIONS

Ahmad, Wasim, et al. (1998), "Alopecia Universalis Associated with a Mutation in the Human hairless Gene," Science, pp. 279, 720.
Bose, Suhira, et al. (1996), "Chaperone Function of Hsp90-Associated Proteins," Science 274, 1715.
Duina, Andrea A., et al. (1996), "A Cyclophilin Function in Hsp90-Dependent Signal Transduction," Science 274, 1713.
Heitman, Joseph H., et al. (1992), "Proline Isomerases at the Crossroads of Protein Folding, Signal Transduction, and Immunosuppression," New Biol. 4:5, 448.

(Continued)

*Primary Examiner*—David Saunders
(74) *Attorney, Agent, or Firm*—Wilmer Cutler Pickering Hale and Dorr LLP

(57) ABSTRACT

The present invention relates to drug screening assays designed to identify non-immunosuppressive agents that modulate hair growth and the use of such agents for modulation of hair growth.

46 Claims, 3 Drawing Sheets

OTHER PUBLICATIONS

Iwabuchi, Tokuro, et al. (1995), J. Dermatol. Sci. 9, 64.

Lane, W.S., et al. (1991), "Complete Amino Acid Sequence of the FK506 and Rapamycin Binding Protein, FKBP, Isolated from Calf Thymus," J. Protein Chem. 10:2, 151.

Maurer, Marcus, et al. (1997), "Hair Growth Modulation by Topical Immunophilin Ligands," Amer. J. Path. 150:4, 1433.

Miyata, Yoshihiko, et al. (1997), "Phosphorlyation of the immunosuppressant FK506-binding protein FKBP52 by casein kinase II: Regulation of HSP90-binding activity of FKBP52," Proc.Natl.Acad.Sci.USA 94, 14500.

Nair, Satish C., et al. (1997), "Molecular Cloning of Human FKBP51 and Comparisons of Immunophilin Interactions with Hsp90 and Progesterone Receptor," Mol.Cell.Biol. 17:2, 594.

Owens-Grillo, Janet K., et al. (1995), "The Cyclosporin A-binding Immunophilin CyP-40 and the FK506-binding Immunophilin hsp56 Bind to a Common Site on hsp90 and Exist in Independent Cytosolic Heterocomplexes with the Untransformed Glucocorticoid Receptor," J.Biol.Chem. 270:35, 20479.

Pratt, William B., et al. (1999), "A Model for the Cytoplasmic Trafficking of Signalling Proteins Involving the hsp90-Binding Immunophilins and $p50^{cdc37}$," Cell.Signal 11:12, 839.

Pratt, William B., et al. (1997), "Steroid Receptor Interactions with Heat Shock Protein and Immunophilin Chaperones," Endoctrine Reviews 18:3, 306.

Sainsbury, T.S.L., et al. (1991), "Differential Effects of FK 506 and Cyclosporine of Hair Regrowth in the DEBR Model of Alopecia Areata," Transplantation Proceedings 23:6, 3332.

Silverstein, Adam, M., et al. (1999), "Different Regions of the Immunophilin FKBP52 Determine Its Association with the Glucocorticoid Receptor, hsp90, and Cytoplasmic Dynein," J.Biol. Chem. 274:52, 36980.

Smith, David F., et al. (1993), "Two FKBP-related Proteins Are Associated with Progesterone Receptor Complexes," J.Biol.Chem. 268:24, 18365.

Yamamoto, Satoshi, et al. (1994), "Stimulation of Hair Growth by Topical Application of FK506, a Potent Immunosuppressive Agent," J.Invest.Dermatol. 102:2, 160.

Yamamoto, Satoshi, et al. (1994), "Hair growth-stimulating effects of cyclosporin A and FK506, potent immunosuppressants," J.Dermatol.Sci. 7(Suppl.), S47.

Bradbury, "Molecular help on the horizon for hair loss?" The Lancet, 2001, pp. 1346, vol. 358, No. 9290.

Gold BG et al. (1999) J. Pharmacol. Exp. Ther. 289:1202.

Hashizume H et al. (1997) J. Dermatol. 36:587.

Pratt WB et al. (1993) J. Steroid Biochem Mol. Biol. 46:269.

Segnitz B and Gehring U (1997) J. Biol Chem 272:18694.

Tai PK et al. (1994) Biochemistry 33:10666.

Tsuji Y et al. (1999) Exp. Dermatol. 8(4):366.

* cited by examiner

| GENES | TISSUES | | |
|---|---|---|---|
| | DERMAL FIBROBLAST | DERMAL PAPILLA | KERATINOCYTE |
| FKBP52 | + | + | + |
| FKBP51 | + | + | + |
| Cyp 40 | + | + | + |

FKBP51/52 AND CYP40-MEDIATED MAMMALIAN HAIR GROWTH

CROSS-REFERENCE TO RELATED APPLICATIONS

This application claims priority to U.S. Provisional Application Ser. No. 60/300,876, filed Jun. 26, 2001, which is incorporated herein by reference in its entirety.

BACKGROUND OF THE INVENTION

1. Field of the Invention

The invention relates to the fields of dermatology, cell biology, and molecular biology. More specifically, the present invention relates to drug screening assays designed to identify non-immunosuppressive agents that modulate hair growth and the use of such agents for modulation of hair growth.

2. Summary of the Related Art

The immunosuppressant drugs FK506, rapamycin and cyclosporin A are well known T-cell specific immunosuppressants that are routinely used to prevent graft rejection in organ transplant patients. In T cells, FK506 and cyclosporin A prevent calcineurin from dephosphorylating the transcription factor NF/AT (nuclear factor of activated T-cells), thereby blocking its translocation into the nucleus and preventing the receptor-mediated increase in synthesis and secretion of cytokines, such as interleukin-2 and, hence, T-cell proliferation (Heitman, J. et al., 1992, *The New Biologist* 4:448–460).

FK506 and cyclosporin A act by binding to endogenous intracellular receptor proteins termed immunophilins. Based on their structure and binding affinity for specific drugs, immunophilins have been divided into two classes of proteins; those proteins having an affinity for FK506 are referred to as FK506-binding proteins (FKBPs), while those having an affinity for cyclosporin are referred to as cyclophilins. Both FKBPs and cyclophilins possess a similar peptidyl-prolyl isomerase activity resulting in cis-trans-isomerization of proteins, which is believed to be important for protein folding and trafficking. In addition, both FKBPs and cyclophilins are characterized by their ability to interact with a variety of different proteins involved in signal transduction.

Several members of the FKBP family have been identified and named according to their calculated molecular mass (Lane, W. S. et al, 1991, *J. Protein Chem.* 10:151–160; U.S. Pat. No. 5,763,590). Cyclophilin A and FKBP12 were originally isolated as cyclosporin A and FK506 binding proteins, respectively, and were shown to exert immunosuppressive activity through inhibition of calcineurin. FKBP-51 was found to be expressed in T-cells where it inhibits calcineurin with much weaker potency, suggesting that multiple immunophilins may participate in mediating FK506 immunosuppressant activity. FKBP-51 has also been shown to be a component of the progesterone receptor complex (Nair, S. C. et al., 1997, *Mol. Cell Biol.* 17:594–603). FKBP52 was initially discovered as a component of the inactive steroid receptor complex (Smith, D. F. et al., 1993, *J. Biol. Chem.* 268:18365–71). The N-terminal domain, residues 1–149 of FKBP52, shares 55% homology with FKBP12, however, it does not have immunosuppressant activity when complexed with FK506. FKBP52 is phosphorylated by casein kinase II and has been found to have chaperone activity independent of isomerase activity (Miyata, Y. et al., 1997, *Proc. Natl. Acad. Sci. USA* 94:14500–14505). CyP40 has only a low affinity for cyclosporin A and is therefore capable of only slight reduction of the immunosuppressive effect of cyclosporin A.

Hsp90 is the most abundant of the heat shock proteins. A number of transcription factors and protein kinases involved in signal transduction are found complexed with hsp90 (Pratt, W. B. et al., 1999, *Cell Signal* 11:839–851; Pratt and Toft, 1997, *Endocrine Rev.* 18:306–360). When complexed with transcription factors, the hsp90 complexes are found to contain high molecular weight immunophilins with tetratricopeptide repeat (TPR) motifs (Duina, A. A. et al., 1996, *Science* 274:1713–1715; Bose, S. et al., 1996, *Science* 274:1715–1717). Such immunophilins include FKBP52 and CyP40 (Owens-Grillo, J. K., 1995, *J. Biol. Chem.* 270: 20479–20484; Miyata, Y. et al., 1997, *Proc. Natl. Acad. Sci. USA* 94:14500–14505; Silverstein, A. M. et al., 1999, *J. Biol. Chem.* 274:36980–36986).

Causes of hair loss include aging, the action of male hormones, the loss of blood supply to hair follicles, and scalp abnormalities. In addition, genetic disposition may account for hair loss. For example, androgenic alopecia is considered to be genetically determined. Recently, a rare autosomal recessive form of hereditary alopecia, referred to as atrichia with papular lesions, was found to result from mutations in the human "hairless" gene (Ahmad, W. et al., 1998, *Science* 279:720–724). In individuals affected with this form of hair loss, hairs are typically absent from the scalp, and patients have very sparse eyebrows and eyelashes. Mutations in the human homolog of the mouse hairless gene lead to congenital alopecia universalis and atrichia with papular lesions. In mice bearing a mutation in the hairless gene, the hair matrix cells appear to undergo premature and massive apoptosis together with a concomitant decline in Bcl-2 expression indicating that the hairless gene product may play a role in regulating cell proliferation, differentiation and apoptosis in the hair follicle. The human hairless gene has recently been isolated and is described in WO 99/38965.

It has been reported that topical application of FK506 and cyclosporin A stimulate hair growth in a dose dependent manner (Sainsbury, T. S. L. et al., 1991, *Transplant. Proc.* 23:3332–3334). For example, FK506 and cyclosporin A have been shown to stimulate hair growth in experimental animals, such as mice and rats (WO 98/55090; Maurer, M., 1997, *Am. J. Path.* 150:1433; Yamamoto, S. et al., 1993, *J. Invest. Dermatol.* 102:160). The effects of FK506 and cyclosporin A and related agents have been described (Tsuji Y. et al., 1999, *Exp. Dermatol.* 8:366–7; McElwee, K. J. et al., 1997, *Br. J. Dermatol.* 137:491–7; Iwabuchi T. et al., 1995, *J. Dermatol. Sci.* 9:64–9; Yamamoto S. and Kato R., 1994, *J. Dermatol. Sci.* 7 *Supp.* 1:547–54; and Yamamoto S. et al., 1994, *J. Invest. Dermatol* 102:160–4).

In addition, Japanese patent application No. 11-174041 describes methods for identifying hair stimulating agents that can bind to immunosuppressive agent-bound proteins that can form a complex with steroid receptors, i.e., FKBP 52 or cyclophilin 40, but do not bind to FKBPs that cannot form complexes with steroid receptors, e.g., FKBP12.

The mechanism of mammalian hair growth stimulated by FK506 and cyclosporin A remains unknown. Despite their potential use as hair stimulating agents, immunosuppressive agents such as FK506 and cyclosporin A also exhibit toxic side effects such as immunosuppression. Thus, there is the need to identify and develop non-immunosuppressive agents that are useful as modulators of hair growth. The present invention is based on the discovery of the signaling pathway by which the immunosuppressive agents FK506 and cyclosporin A modulate hair growth. This discovery provides drug screening assays for identification of non-immunosuppressive agents capable of modulating hair growth.

3. SUMMARY OF THE INVENTION

The present invention relates to drug screening assays designed to identify non-immunosuppressive agents that modulate hair growth and the use of such agents for modulation of hair growth. The invention is based on the discovery of the signal transduction pathway by which specific immunophilins, namely FKBP51 and FKBP52, and CyP40, modulate hair growth. As disclosed herein, the FKBP51/52 proteins are found to be expressed in hair follicle dermal papillae. In addition, FKBP51/52 are found complexed with the hsp90, Gli3, AFX-1 and hairless protein within the cell. Contact of dermal papillae cells with FK506 or cyclosporin A was also found to stimulate expression of the Gli3 target gene, BMP4 and HNF3β. The pathway of the invention serves as a basis for methods designed to identify non-immunosuppressive agents which can be used to modulate hair growth.

The invention relates to assays designed to screen for agents that modulate the components of the FKBP51/52 and CyP40 signal transduction pathway, i.e., agents that act as agonists or antagonists of such components, including FKBP51/52, CyP40, hsp90, Gli3, AFX-1 and/or the hairless protein. In an embodiment of the invention, a method is provided for rational drug design of agents which specifically modulate activity and/or the association of FKBP51/52 or CyP40 with the hsp90, hairless, AFX-1 and/or Gli3 protein. The present invention further provides cell based and non-cell based assays for identifying agents which modulate the interaction and/or activity of the components of the inventive pathway, i.e., the FKBP51/52, CyP40, hsp90, Gli3 AFX-1 and hairless protein.

Specifically, the invention provides a method for identifying a compound capable of modulating hair growth comprising:
  (i) contacting a cell that expresses, or a preparation containing, FKBP51/52 or CyP40, hsp90 and a protein selected from the group consisting of hairless, AFX-1, and gli3, with a test compound;
  (ii) determining the level of complex formation between FKBP51/52 or CyP40, hsp90 and at least one protein selected from the group consisting of the hairless, AFX-1, and gli3, in the cell, or preparation, contacted with the test compound; and
  (iii) comparing the level of complex formation obtained in (ii) to the level of complex formation between FKBP51/52 or CyP40, hsp90, and at least one protein selected from the group consisting of the hairless, AFX-1, and gli3, in the absence of test compound;

wherein a difference in the level of complex formation in the presence versus in the absence of test compound has a positive correlation with hair growth modulating activity.

As used herein, the term "preparation" refers to a composition comprising at least one cellular component that has been isolated, extracted or partially purified either from a cell in which it is naturally expressed or from a cell which has been genetically engineered to express the component, or a component that has been synthetically prepared, which composition can be used to carry out the recited method. Such preparations include, but are not limited to, cell fractions prepared by standard techniques, as well as aqueous, buffered solutions of cellular components prepared by combining together previously synthesized or purified components.

As used herein, the phrase "positive correlation with hair growth modulating activity" refers to an observation of the biological activity of a test compound wherein the activity indicates that the test agent is capable of either stimulating or inhibiting hair growth.

In another embodiment of the invention, a method is provided for identifying a compound capable of modulating hair growth comprising:
  (i) contacting a cell that expresses a nuclear hormone receptor and a reporter gene under the transcriptional control of a hairless, AFX-1, or gli3 gene responsive element with a test compound and measuring the level of reporter gene expression in the cell;
  (ii) measuring the level of reporter gene expression in the absence of the test compound; and
  (iii) comparing the levels of reporter gene expression measured in (i) and (ii);

wherein a difference in the levels of reporter gene expression measured in steps (i) and (ii) has a positive correlation with hair growth modulating activity of the test compound.

The invention further provides a method for identifying a compound capable of promoting hair growth comprising:
  (i) contacting a sample containing a hairless, AFX-1 or gli3 gene product with a test compound;
  (ii) determining whether the test compound binds to the hairless, AFX-1 or gli3 gene product; and
  (iii) determining whether the test compound inhibits complex formation between the hairless, AFX-1 or gli3 gene product and a binding partner selected from the group consisting of FKBP51/52, CyP40, a nuclear hormone receptor, a hsp90 protein, and a combination thereof;

wherein the ability of a test compound to both bind to the hairless, AFX-1 or gli3 gene product and inhibit complex formation has a positive correlation with hair growth promoting activity.

The invention further relates to a method for identifying a compound capable of modulating hair growth comprising:
  (i) contacting a cell that expresses FKBP51/52 or CyP40, and hsp90, a nuclear hormone receptor, and the hairless, AFX-1 or gli3 gene product with a test compound in the presence of a nuclear hormone receptor ligand;
  (ii) determining the level of nuclear translocation of the hairless, AFX-1 or gli3 gene product into the nucleus of the cell;
  (iii) determining the level of nuclear translocation in the absence of the test compound; and
  (iv) comparing the level of nuclear translocation measured in (ii) and (iii);

wherein a difference in the level of nuclear translocation measured in steps (ii) and (iii) has a positive correlation with hair growth modulating activity of the test compound.

Identified agents can be used to modulate hair growth. Such agents are particularly useful for treating baldness resulting from genetic factors, aging, local skin conditions and diseases that affect the body generally, i.e., systemic diseases. Such disorders include, but are not limited to, male pattern baldness, female pattern baldness, toxic baldness, alopecia greata and scarring alopecia. In addition, the agents can be used to treat subjects with hair loss associated with radiation or chemotherapy.

Thus, the invention encompasses a method for modulating hair growth in a mammal comprising administering to the mammal a compound that modulates complex formation between FKBP51/52, CyP40 or hsp90 and at least one protein selected from the group consisting of hairless, gli3, AFX-1, and hsp90.

The invention provides a method for modulating hair growth in a mammal comprising administering to the mammal a compound that modulates the nuclear translocation of a protein selected from the group consisting of the hairless, AFX-1 and gli3 protein.

In yet another embodiment of the invention, a method is provided for modulating hair growth in a mammal comprising administering to the mammal a compound that modulates hairless, AFX-1-or gli-3-mediated gene expression.

4. DESCRIPTION OF THE FIGURES

The foregoing and other objects of the present invention, the various features thereof, as well as the invention itself may be more fully understood from the following description, when read together with the accompanying drawings in which.

5. DETAILED DESCRIPTION

Figures 1, 2:
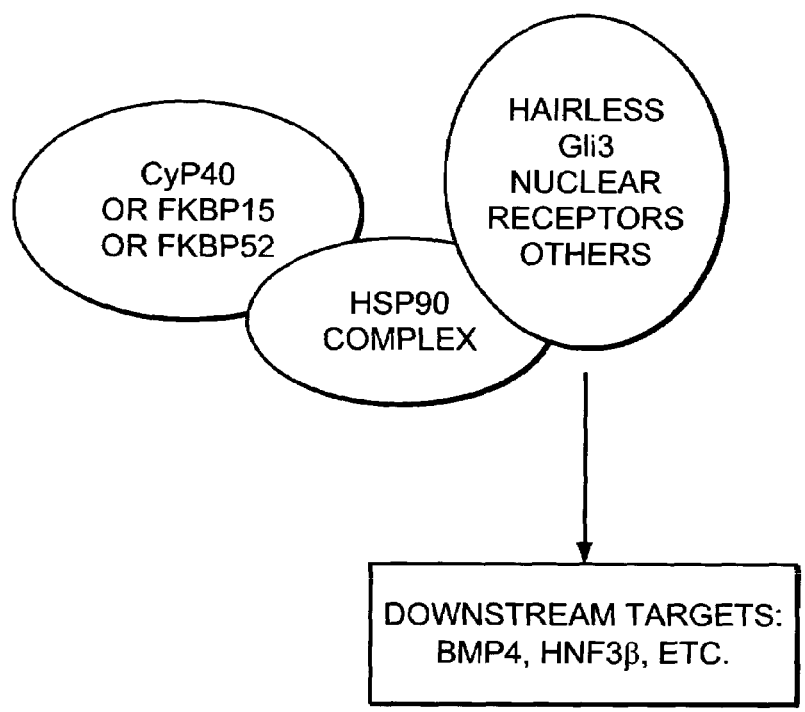
FIG. 1 is a schematic representation depicting the proposed model of interactions between FKBP51/52, CyP40, steroid receptors, hsp 90 and other binding partners.
FIG. 2 is a representation of RT-PCR analysis of human dermal papilla RNA, demonstrating that in cultured human dermal papilla cells, expression of FKBP51, FKBP52 and CyP40 is detected using RT-PCR.

The present invention is based on the discovery of the signal transduction pathway by which specific immunophilins, namely FKBP51, FKBP52 and CyP40, modulate hair growth. The discovery of the pathway by which agents such as FK506 and cyclosporin A modulate hair growth provides screening targets for agents that can be used to promote hair growth while having a reduced effect on the immune system.

The present invention encompasses assays designed to identify agents that modulate the interaction and/or activity of the components of the signal transduction pathway. Such components include, for example, the FKBP51/52, CyP40, hsp90, Gli3, AFX-1 and hairless proteins. Both cell based and non-cell based assays can be used to identify agents that either increase or decrease the activity of the FKBP51/52 and CyP40 signal transduction pathway. The present invention further provides for rational drug design of agents that specifically promote or inhibit association of FKBP51/52 or CyP40 with the hsp90, hairless, AFX-1 and/or Gli3 proteins.

In other embodiments, the present invention provides for agents designed or identified by the foregoing methods. Further, the present invention provides for the use of said agents for enhancement of hair growth. In particular, such agents can be used to treat baldness which can result from genetic factors, aging, and/or local skin conditions.

5.1 Screening Assays for Agents Useful in Modulating the Activity of FKBP51/52/CyP40

The present invention relates to screening assay systems designed to identify agents or compositions that modulate FKBP51/52 or CyP40 activity or FKBP51/52 or CyP40 gene expression, and thus, may be useful for modulation of hair growth.

5.1.1 Recombinant Expression of Proteins Involved in Hair Growth

For purposes of developing screening assays designed to identify agents or compositions that modulate hair growth, it may be necessary to recombinantly express the FKBP51/52 or CyP40 proteins and/or the proteins that interact with FKBP51/52, and CyP40, i.e., hsp90, Gli3, AFX-1 and hairless proteins. The cDNA sequences and deduced amino acid sequences of FKBP51 (SEQ ID NOS: 8 and 9) and FKBP52 (SEQ ID NOS: 10 and 11) have been characterized. The term FKB51/52 as used herein refers to either or both the FKBP51 and FKBP52 proteins. The cDNA sequence and deduced amino acid sequences of CyP40 have been characterized (SEQ ID NOS: 12 and 13). The cDNA sequences and deduced amino acid sequences of hsp90, Gli3, AFX-1 and hairless have also been characterized: SEQ ID NOS: 14 and 15 (hairless); SEQ ID NOS: 16 and 17 (Gli3), SEQ ID NOS: 18 and 19 (hsp90); and SEQ ID NOS: 20 and 21 (AFX-1). For simplicity, recombinant expression is described below for FKBP51/52; however, the methods can also be utilized for recombinant expression of CyP40, hsp90, Gli3, AFX-1 and/or the hairless protein.

FKBP51/52 nucleotide sequences can be isolated using a variety of different methods known to those skilled in the art. For example, a cDNA library constructed using RNA from a tissue known to express FKBP51/52 can be screened using a labeled FKBP51/52 specific probe. Alternatively, a genomic library can be screened to derive nucleic acid molecules encoding the FKBP51 or FKBP52 protein. Further, FKBP51/52 nucleic acid sequences can be derived by performing a polymerase chain reaction (PCR) using two oligonucleotide primers designed on the basis of known FKBP51/52 nucleotide sequences. The template for the reaction can be cDNA obtained by reverse transcription of mRNA prepared from cell lines or tissue known to express FKBP51/52.

FKBP51/52 protein, polypeptides and peptide fragments, mutated, truncated or deleted forms of FKBP51/52 and/or FKBP51/52 fusion proteins can be prepared for a variety of uses, including, but not limited to, the identification of other cellular gene products involved in the regulation of FKBP51/52-mediated hair growth, and the screening for agents that can be used to modulate hair growth. FKBP51/52 fusion proteins include fusions to an enzyme, fluorescent protein, and a polypeptide tag or luminescent protein, all of which provide a marker function.

While the FKBP51/52 polypeptides and peptides can be chemically synthesized (e.g., see Creighton, 1983, *Proteins: Structures and Molecular Principles*, W.H. Freeman & Co., N.Y.), large polypeptides derived from FKBP51/52 and the full length FKBP51/52 proteins can be advantageously produced by recombinant DNA technology using techniques well known in the art for expressing nucleic acids containing FKBP51/52 gene sequences and/or other coding sequences. Such methods can be used to construct expression vectors containing the FKBP51/52 nucleotide sequences and appropriate transcriptional and translational control signals. These methods include, for example, in vitro recombinant DNA techniques, synthetic techniques, and in vivo genetic recombination. (See, for example, the techniques described in Sambrook et al., 1989, *Molecular Cloning, A Laboratory Manual*, Cold Spring Harbor Press, N.Y.; and Ausubel et al., 1989, *Current Protocols in Molecular Biology*, Green Publishing Associates and Wiley Interscience, N.Y.).

A variety of host-expression vector systems can be utilized to express the FKBP51/52 nucleotide sequences (See, e.g., U.S. Pat. No. 5,763,590 for expression of FKBP 52). Where the FKBP51/52 peptide or polypeptide is expressed as a soluble derivative and is not secreted, the peptide or polypeptide can be recovered from the host cell. Alternatively, where the FKBP51/52 peptide or polypeptide is secreted, the peptide or polypeptides can be recovered from the culture media.

The expression systems that can be used for purposes of the invention include, but are not limited to, microorganisms such as bacteria transformed with recombinant bacteriophage, plasmid or cosmid DNA expression vectors containing FKBP51/52 encoding nucleotide sequences, yeast transformed with recombinant yeast expression vectors containing FKBP51/52 encoding nucleotide sequences or mammalian cell systems, or insect cell systems containing FKBP51/52 recombinant expression constructs containing promoters derived from the genome of mammalian or insect cells or from mammalian or insect viruses.

Appropriate expression systems can be chosen to ensure that the correct modification, processing, and sub-cellular localization of the FKBP51/52 protein occurs. To this end, eukaryotic host cells that possess the ability to properly modify and process the FKBP51/52 protein are preferred. For long-term, high yield production of recombinant FKBP51/52 protein, such as that desired for development of cell lines for screening purposes, stable expression is preferred. Rather than using expression vectors which contain origins of replication, host cells can be transformed with DNA controlled by appropriate expression control elements and a selectable marker gene, e.g., tk, hgprt, dhfr, neo, and hygro genes, to name a few. Following the introduction of the foreign DNA, engineered cells may be allowed to grow for 1–2 days in enriched media, and then switched to a selective media. Such engineered cell lines can be particularly useful in screening and evaluating agents that modulate the endogenous activity of the FKBP51/52 gene product.

In addition, in some instances it may be necessary to co-express interactive binding proteins such as the CyP40, hsp90, Gli3, AFX-1 and hairless proteins for use in the screening assays of the invention. Methods described above for expression of FKBP51/52 can be similarly used to co-express such binding proteins.

5.1.2 Non-Cell Based Assays

In accordance with the invention, non-cell based assay systems can be used to identify agents that interact with, i.e., bind to, FKBP51/52 or CyP40, and regulate the activity of such proteins. Such agents may act as antagonists or agonists of FKBP51/52 or CyP40 activity and can be used to regulate hair growth. In particular, such agents may function to disrupt or prevent the formation of a complex between FKBP51/52 or CyP40 and their binding partners, i.e., the hsp90, Gli3, AFX-1 and/or hairless protein. For simplicity, the non-cell based assays are described below for FKBP51/52; however, they can be similarly utilized for CyP40 as well.

Recombinant FKBP51/52, including peptides corresponding to different functional domains, or FKBP51/52 fusion proteins, can be expressed and used in assays to identify agents that interact with FKBP51/52.

To this end, soluble FKBP51/52 can be recombinantly expressed and utilized in non-cell based assays to identify agents that bind to FKBP51/52. Recombinantly expressed FKBP51/52 polypeptides or fusion proteins containing one or more of the FKBP51/52 functional domains can be prepared as described above, and used in the non-cell based screening assays. One such functional domain is the tetratricopeptide repeat (TPR) which is important for protein/protein interactions. For example, the full length FKBP51/52, or a soluble truncated FKBP51/52, e.g., in which one or more domains is deleted from the molecule but the TPR is retained, a peptide corresponding to the TPR motifs, or a fusion protein containing the FKBP51/52 TPR motif fused to a protein or polypeptide that affords advantages in the assay system (e.g., for labeling or isolating the resulting complex) can be utilized. Where agents that interact with the TPR motif are sought to be identified, peptides corresponding to the FKBP51/52 TPR motif and fusion proteins containing the FKBP51/52 TPR motif can be used. The FKBP51/52 protein can also be present as part of a crude or semi-purified extract.

The principle of the assays used to identify agents that bind to FKBP51/52 involves preparing a reaction mixture of FKBP51/52 and the test agent under conditions and for time sufficient to allow the two components to interact and bind, thus forming a complex which can be removed and/or detected in the reaction mixture. The identity of the bound test agent is then determined.

The screening assays are accomplished by any of a variety of commonly known methods. For example, one method to conduct such an assay involves anchoring the FKBP51/52 protein, polypeptide, peptide, fusion protein, or the test substance onto a solid phase and detecting FKBP51/52/test agent complexes adhered to the solid phase at the end of the reaction. In one embodiment of such a method, the FKBP51/52 reactant is anchored onto a solid surface, and the test agent, which is not anchored, may be labeled, either directly or indirectly.

In practice, microtitre plates conveniently can be utilized as the solid surface. The anchored component is immobilized to the solid surface by non-covalent or covalent attachment. The solid surfaces may be prepared in advance and stored. In order to conduct the assay, the non-immobilized component is added to the solid surface coated with the anchored component. After the reaction is completed, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes have been formed. Where the previously non-immobilized component is not pre-labeled, an indirect label can be used to detect complexes on the solid surface, e.g., using a labeled antibody specific for the previously non-immobilized component.

Alternatively, a reaction is conducted in a liquid phase, the reaction products are separated from unreacted components using an immobilized antibody specific for FKBP51/52 protein, fusion protein or the test agent, and complexes are detected using a labeled antibody specific for the other component of the complex.

In accordance with the invention, non-cell based assay systems can be used to identify agents that directly interfere with the interaction between FKBP 51/52 and one or more other proteins within the cell. The proteins that interact with the FKBP51/52 are referred to, for purposes of this discussion, as "binding partners." These binding partners are likely to be involved in the FKBP51/52 signal transduction pathway. Such binding partners include, but are not limited to, the hsp90, Gli3, AFX-1 and hairless protein. Therefore, it is desirable to identify agents that modulate the interaction of one or more of such binding partners with FKBP51/52. Such agents may interfere with or disrupt the interaction of one or more such binding partners with FKBP51/52 and may be useful in modulating hair growth. Alternatively, agents can be identified that increase the affinity or improve the interaction between the one or more binding partners and FKBP51/52.

The basic principle of the assay systems used to identify agents that interfere with the interaction between a FKBP51/52 moiety and one or more of its binding partners involves preparing a reaction mixture containing FKBP51/52 protein, polypeptide, peptide or fusion protein, and the one or more binding partner, and incubating the reaction mixture under conditions and for a time sufficient to allow the components to interact and bind, thus forming a complex. In order to test an agent for inhibitory activity, the reaction mixture is prepared both in the presence and absence of the test agent. The test agent may be initially included in the reaction mixture, or may be added at a time subsequent to the addition of the FKBP51/52 moiety with its binding partner(s). Control reaction mixtures are incubated without the test agent or with a placebo. The formation of any complexes between the FKBP51/52 moiety and the binding partner(s) is then detected. The formation of a complex in the control reaction, but not in the reaction mixture containing the test agent, indicates that the test agent interferes with the interaction of the FKBP51/52 and the interactive binding partner(s).

The assay for agents that interfere with the interaction of FKBP51/52 and binding partners can be conducted in a heterogeneous or homogeneous format. Heterogeneous assays involve anchoring either the FKBP51/52 moiety product or the binding partner onto a solid surface and detecting complexes attached to the solid surface at the end of the reaction. In homogeneous assays, the entire reaction is carried out in a liquid phase. In either approach, the order of addition of reactants can be varied to obtain different information about the agents being tested. For example, test agents that interfere with the interaction by competition can be identified by conducting the reaction in the presence of the test substance, i.e., by adding the test substance to the reaction mixture prior to or simultaneously with FKBP51/52 moiety and interactive binding partner. Alternatively, test agents that disrupt preformed complexes, e.g. agents with higher binding constants that displace one of the components from the complex, can be tested by adding the test agent to the reaction mixture after complexes have been formed. The various formats are described briefly below.

In a particular embodiment, an FKBP51/52 fusion can be prepared for immobilization. For example, the FKBP51/52 or a peptide fragment, e.g., corresponding to the TPR motif, can be fused to a glutathione-S-transferase (GST) gene using a fusion vector, such as pGEX-5X-1, in such a manner that its binding activity is maintained in the resulting fusion protein. The interactive binding partner, i.e., the hsp90, Gli3, AFX-1 or hairless protein, can be purified and used to raise a monoclonal antibody, using methods routinely practiced in the art. The generation of monoclonal antibodies can be omitted if such antibodies exist and are publicly available. This antibody can be labeled with the radioactive isotope $^{125}$I, for example, by methods routinely practiced in the art. In a heterogeneous assay, for example, the GST-FKBP51/52 fusion protein can be anchored to glutathione-agarose beads. The interactive binding partner can then be added in the presence or absence of the test agent in a manner that allows interaction and binding to occur. At the end of the reaction period, unbound material can be washed away, and the labeled monoclonal antibody can be added to the system and allowed to bind to the complexed components. The interaction between the FKBP51/52 gene product and the interactive binding partner can be detected by measuring the amount of radioactivity that remains associated with the glutathione-agarose beads. A successful inhibition of the interaction by the test agent will result in a decrease in measured radioactivity.

Alternatively, the GST-FKBP51/52 fusion protein and the interactive binding partner can be mixed together in liquid in the absence of the solid glutathione-agarose beads. The test agent can be added either during or after the species are allowed to interact. This mixture can then be added to the glutathione-agarose beads and unbound material is washed away. Again, the extent of inhibition of the FKBP51/52 binding partner interaction can be detected by adding the labeled antibody and measuring the radioactivity associated with the beads.

In alternate embodiments of the invention, a homogeneous assay can be used. In this approach, a preformed complex of the FKBP51/52 moiety and the interactive binding partner is prepared in which either the FKBP51/52 or its binding partner is labeled, but the signal generated by the label is quenched due to formation of the complex. The addition of a test substance that competes with and displaces one of the species from the preformed complex will result in the generation of a signal above background. In this way, test substances which disrupt FKBP51/52 binding partner interaction can be identified.

In accordance with the invention, non-cell based assays can also be used to screen for agents that directly inhibit enzymatic activities associated with FKBP51/52. Such activities include, but are not limited to, proline isomerase activity. For example, a peptidyl-prolyl cis-trans isomerase assay performed according to Harrison and Stein (1980, *Biochem.* 29:3813–3816) with modifications described by Park et al. (1992, *Biol. Chem.* 267:3316–3324) can be used to measure the level of FKBP51/52 activity. To this end, a reaction mixture of FKBP51/52 and a test agent is prepared in the presence of substrate, and the enzymatic activity of FKBP51/52 is compared to the activity observed in the absence of test agent.

In non-limiting embodiments of the invention, a reaction mixture of FKBP51/52, a test agent and substrate is prepared and the enzymatic activity of FKBP51/52 is compared to the activity observed in the absence of the test agent, wherein a decrease in the level of FKBP51/52 enzymatic activity in the presence of the test agent indicates that an inhibitor of FKBP51/52 has been identified. Alternatively, a reaction mixture of FKBP51/52, a test agent and substrate is prepared and the enzymatic activity of FKBP51/52 is compared to the activity observed in the absence of the test agent, wherein an increase in the level of FKBP51/52 enzymatic activity in the presence of the test agent indicates that a FKBP51/52 agonist has been identified.

5.1.3 Cell Based Assays

In accordance with the invention, cell based assay systems can be used to identify agents that regulate the activity of FKBP51/52 or CyP40. In addition, it is believed that the FKBP51/52/hsp90/hairless/AFX-1/gli3 complex or CyP40/hsp90/hairless/AFX-1/gli3 is bound to nuclear hormone receptors within the cell. Thus, the cell based assays may be performed using cells expressing a nuclear hormone receptor. Such nuclear hormone receptors include, but are not limited to, androgen, vitamin D, retinoic acid, aryl hydrocarbon and thyroid hormone receptors. When using such cells, the activity of a test agent can be tested in the presence or absence of a nuclear hormone receptor ligand. Cell based assays are described below for identification of agents that regulate the activity of FKBP51/52 proteins; however, such cell based assays may be used to similarly identify agents that regulate the activity of CyP40.

The present invention provides methods for identifying an agent that activates FKBP51/52 enzymatic activity comprising (i) contacting a cell expressing FKBP51/52 with a test agent and measuring the level of FKBP51/52 enzymatic activity; (ii) in a separate experiment, contacting a cell expressing FKBP51/52 protein with a vehicle control and measuring the level of FKBP51/52 enzymatic activity where the conditions are essentially the same as in part (i), and then (iii) comparing the level of FKBP51/52 activity measured in part (i) with the level of FKBP51/52 activity in part (ii), wherein an increased level of FKBP51/52 enzymatic activity in the presence of the test agent compared to the level of FKBP51/52 enzymatic activity in the presence of vehicle control indicates that the test agent is a FKBP51/52 enzyme activator.

The present invention also provides methods for identifying an agent that inhibits FKBP51/52 enzymatic activity comprising (i) contacting a cell expressing FKBP51/52 with a test agent in the presence of FK506 and measuring the level of FKBP51/52 enzymatic activity; (ii) in a separate experiment, contacting a cell expressing FKBP51/52 in the presence of FK506 and measuring the level of FKBP51/52 enzymatic activity, where the conditions are essentially the same as in part (i); and then (iii) comparing the level of FKBP51/52 enzymatic activity measured in part (i) with the level of FKBP51/52 enzymatic activity in part (ii), wherein a decrease in the level of FKBP51/52 enzymatic activity in the presence of the test agent compared to the level of FKBP51/52 enzymatic activity in the presence of vehicle control indicates that the test agent is a FKBP51/52 enzyme inhibitor.

In utilizing such cell systems, the cells expressing the FKBP51/52 protein are exposed to a test agent or to a vehicle control (e.g., placebo). After or during exposure, the cells can be assayed to measure the enzymatic activity of FKBP51/52 or the activity of the FKBP51/52 dependent signal transduction pathway itself.

The ability of a test molecule to modulate the enzymatic activity of FKBP51/52 can be measured using standard biochemical and physiological techniques, e.g., as measured by a chemical, physiological, biological or phenotypic change, induction of a host cell gene or reporter gene, change in host cell kinase activity, etc. For example, FKBP51/52 associated peptidyl-prolyl isomerase activity can be measured. Assays for such activity include those described in Harrison and Stein (1980, *Biochem,* 29:3813–3816); Park, S. T. et al., (1992, *J. Biol. Chem.* 267:3316–3324); and U.S. Pat. No. 5,763,590. Alternatively, the expression of genes known to be modulated by activation of the FKBP51/52 signal transduction pathway, such as BMP4 or HNF3β, can be assayed to identify modulators of FKBP51/52 or activity.

In addition, animal models can be utilized to identify agents capable of ameliorating hair loss. Such animal models can be used as test substrates for the identification of drugs, pharmaceuticals, therapies and interventions that can be effective in treating such disorders. For example, animal models can be exposed to an agent suspected of exhibiting an ability to modulate hair growth at a sufficient concentration and for a time sufficient to elicit such hair growth in the exposed animals. The response of the animals to the exposure can be monitored by assessing the modulation of hair growth. In a specific embodiment of the invention, a C3H mouse model can be used to measure the capacity of a test compound to initiate hair growth. Typically, approximately seven-week-old female C3H mice are used for experiments. The lower back hair of mice are sheared with an electrical clipper, followed by administration of the test agent. Visual observation of the test animals' hair growth will result in a determination regarding the ability of a test agent to modulate hair growth. In addition, the Dundee Bald rat model animal or chemotherapy treated mice can be used. With regard to intervention, any treatments which reverse any aspect of disorder-like symptoms should be considered as candidates for human therapeutic intervention. Dosages of test agents may be determined by deriving dose-response curves, as discussed below.

5.2 Rational Drug Design

In an embodiment of the invention, computer modeling and searching technologies can be used for identification of agents that can modulate the protein interactions between FKBP51/52, CyP40, hsp90, Gli3, AFX-1 and/or hairless protein. For example, based on the knowledge of the FKBP51/52 or CyP40 binding sites and the study of complexes between FKBP51/52 or CyP40 and proteins such as hsp90, Gli3, AFX-1 and hairless, potential modulators of the FKBP51/52 or CyP40 signal transduction pathway can be identified.

The three dimensional geometric structure of binding sites can be determined using known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures may be measured with a complexed protein or agent, which may increase the accuracy of the active site structure determined.

If an incomplete or insufficiently accurate structure is determined, the methods of computer based numerical modeling can be used to complete the structure or improve its accuracy. Any recognized modeling method may be used, including parameterized models specific to particular biopolymers such as proteins, molecular dynamic models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Having determined the structure of the binding site, either experimentally, by modeling, or by a combination of such methods, candidate modulating agents can be identified by searching databases containing agents along with information on their molecular structure. Such a search seeks agents having structures that match the determined binding site structure and that interact with the groups defining the active site. Such a search can be manual, but is preferably computer assisted. Agents found from this search are potential hair growth modulating agents.

Alternatively, these methods can be used to modify known hair growth modulating agents to improve their activity. A known agent can be modified and the structural effects of modification can be determined using the experimental and computer modeling methods described above. The altered structure can then be compared to the active site structure of the agent to determine if an improved fit or interaction results. In this manner, systematic variations in composition, such as by varying side groups, can be quickly evaluated to obtain modified modulating agents or ligands of improved specificity or activity, e.g., modifying cyclosporin A to increase its affinity to CyP40 while reducing its affinity to cyclosporin A or B.

Further experimental and computer modeling methods useful to identify modulating agents based upon identification of the binding sites of FKBP51/52 or FKBP51/52 binding proteins will be apparent to those of skill in the art. In addition, experimental and computer modeling methods useful to identify modulating agents based upon identification of the binding sites of CyP40 or CyP40 binding proteins will be apparent to those of skill in the art.

Examples of molecular modeling systems are the CHARMm and QUANTA programs (Polygen Corporation, Waltham, Mass.). CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988, *Acta Pharmaceut. Fennica* 97:159–166; Ripka, 1988, *New Scientist* 54–57; McKinaly and Rossmann, 1989, *Ann. Rev. Pharmacol. Toxiciol.* 29:111–122; Perry and Davies, 1989, *OSAR: Quantitative Structure-Activity Relationships in Drug Design*, pp. 189–193 (Alan R. Liss, Inc.); Lewis and Dean, 1989 *Proc. R. Soc. Lond.* 236:125–140 and 141–162; and, with respect to a model receptor for nucleic acid components, Askew, et al., 1989, *J. Am. Chem. Soc.* 111: 1082–1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). As described herein, FKBP51/52 bind to a number of known transcription factors, including, but not limited to, AFX-1, gli3 and hairless protein. Thus, although the modeling described above is primarily designed for application to drugs specific to particular proteins, they can be adapted to design of drugs specific to regions of DNA or RNA, once that region is identified.

5.3 Assay for Agents that Regulate the Expression of FKBP51/52 or CyP40

In accordance with the invention, a cell based assay system can be used to screen for agents that modulate the expression of FKBP51/52 or CyP40 within a cell. Assays can be designed to screen for agents that regulate FKBP51/52 or CyP40 expression at either the transcriptional or translational level. The assays described below are designed for identification of agents capable of regulating FKBP51/52 gene expression; however, such assays can be similarly used to identify agents that regulate CyP40 gene expression.

In one embodiment, DNA encoding a reporter molecule can be linked to a regulatory element of the FKBP51/52 gene and used in appropriate intact cells, cell extracts or lysates to identify agents that modulate FKBP51/52 gene expression. Such reporter molecules include, but are not limited to, chloramphenicol acetyltransferase (CAT), luciferase, β-glucuronidase (GUS), growth hormone, or placental alkaline phosphatase. Such constructs are introduced into cells, thereby providing a recombinant cell useful for screening assays designed to identify modulators of FKBP51/52 gene expression.

Following exposure of the cells to the test agent, the level of reporter gene expression can be quantitated to determine the test agent's ability to regulate FKBP51/52 expression. Alkaline phosphatase assays are particularly useful in the practice of the invention where the enzyme is secreted from the cell, and tissue culture supernatant can then be assayed for secreted alkaline phosphatase. In addition, alkaline phosphatase activity can be measured by calorimetric, bioluminescent or chemiluminescent assays such as those described in Bronstein, I. et al., 1994, *Biotechniques* 17:172–177. Such assays provide a simple, sensitive, easily automatable detection system for pharmaceutical screening.

To identify agents that regulate FKBP51/52 translation, cells or in vitro cell lysates containing FKBP51/52 transcripts can be tested for modulation of FKBP51/52 mRNA translation. To assay for inhibitors of FKBP51/52 translation, test agents are assayed for their ability to modulate the translation of FKBP51/52 mRNA in in vitro translation extracts.

In an embodiment of the invention, the level of FKBP51/52 expression can be modulated using antisense or ribozyme approaches to inhibit or prevent translation of FKBP51/52 mRNA transcripts, or triple helix approaches to inhibit transcription of the FKBP51/52 gene. Such approaches can be utilized to modulate hair growth.

Antisense approaches involve the design of oligonucleotides (either DNA or RNA) that are complementary to at least a portion of FKBP51/52 mRNA. The antisense oligonucleotides bind to the complementary mRNA transcripts and prevent translation. Absolute complementarity, although preferred, is not required. One skilled in the art can ascertain a tolerable degree of mismatch by use of standard procedures to determine the melting point of the hybridized complex.

In yet another embodiment of the invention, ribozyme molecules designed to catalytically cleave FKBP51/52 mRNA transcripts can be used to prevent translation of FKBP51/52 mRNA and expression of FKBP51/52. (See, e.g., PCT International Publication WO 90/11364, published Oct. 4, 1990; Sarver et al., 1990, *Science* 247:1222–1225).

Alternatively, endogenous FKBP51/52 gene expression can be reduced by targeting deoxyribonucleotide sequences complementary to the regulatory region of the FKBP51/52 gene (i.e., the FKBP51/52 promoter and/or enhancers) to form triple helical structures that prevent transcription of the FKBP51/52 gene in targeted cells in the body. (See generally, Helene, C. et al., 1991, *Anticancer Drug Des.* 6:569–584; and Maher, LJ, 1992, *Bioassays* 14:807–815).

The oligonucleotides of the invention, i.e., antisense, ribozyme, and triple helix forming oligonucleotides, can be synthesized by standard methods known in the art, e.g., by use of an automated DNA synthesizer (such as are commercially available from Biosearch, Applied Biosystems, etc.). Alternatively, recombinant expression vectors can be constructed to direct the expression of the oligonucleotides of the invention. Such vectors can be constructed by recombinant DNA technology methods standard in the art. In a specific embodiment, vectors such as viral vectors can be designed for gene therapy applications where the goal is in vivo expression of inhibitory oligonucleotides in targeted cells.

5.4 Assay for Agents that Regulate the Transcriptional Activity of the Gli3 AFX-1 and/or Hairless Transcription Factors In accordance with the invention, assays can be developed to identify agents that modulate transcriptional activation mediated by FKBP51/52, CyP40, Gli3, AFX-1 and the hairless protein. While not being bound to any one particular theory, it is believed that the binding of FK506 to the FKBP51/52/hsp90 complex, or cyclosporin A to the CyP40/hsp90 complex, promotes the activation and/or release of the zinc finger transcription factors hairless and/or Gli3 from the complex. Nuclear translocation of the hairless and/or Gli3 proteins results in transactivation of target genes and stimulation of hair production.

In accordance with the invention, an assay can be used to identify agents that modulate translocation of the Gli-3, AFX-1 and/or hairless protein into the nucleus. For purposes of the assay, the hairless, AFX-1 and/or Gli3 protein can be tagged with an easily detectable peptide tag such as GFP. Such an assay involves contacting a cell expressing a tagged hairless, AFX-1 or Gli3 protein with a test agent in the presence of FK506 or cyclosporin A. Alternatively, the assay can be performed using a cell expressing a nuclear hormone receptor in the presence of nuclear hormone receptor ligand. Following exposure to the test agent, the amount of tagged hairless, AFX-1 or Gli3 protein located within the nucleus is measured, e.g., by measuring the amount of tagged protein present in the nucleus. If the amount of tagged protein detected in the nucleus is decreased in the presence of the test agent, as compared to the same assay conducted in the presence of a vehicle control, a modulator of hairless and/or Gli3 nuclear translocation has been identified.

In addition, cells expressing Gli3, AFX-1 or hairless tagged proteins can be used to assay for agents that modulate the dissociation of hairless, AFX-1 and/or Gli3 from the FKBP51/52/hsp90 or CyP40/hsp90 complexes. Such assays can be done in the presence of FK506 or cyclosporin A to identify agents that inhibit the FK506- or cyclosporin A-mediated dissociation of hairless, AFX-1 and/or Gli3 from said complexes. For example, a cell expressing a tagged hairless, AFX-1 or Gli3 protein is contacted with a test agent in the presence of FK506. Following contact with the test agent, a cell lysate can be prepared followed by immunoprecipitation of the FKBP51/52 or CyP40 protein complex. The immunoprecipitated complex is then analyzed to determine the presence or absence of the tagged Gli3, AFX-1 or hairless protein.

Downstream target genes of the Gli3 transcription factor are regulated by FK506 and cyclosporin A treatment. For example, BMP4 is a downstream target gene of the Gli3 pathway and expression of BMP4 is stimulated in the presence of FK506 and cyclosporin A. Thus, in a specific embodiment of the invention, constructs containing a Gli3 responsive element, e.g., 5'TGGGTGGTC-3', can be linked to any of a variety of different reporter genes and introduced into cells expressing FKBP51/52. Such reporter genes, as set forth above, can include, but are not limited to, those encoding chloramphenicol acetyltransferase (CAT), luciferase, GUS, growth hormone, or placental alkaline phosphatase. Following exposure of the cells to the test agent, the level of reporter gene expression can be quantitated to determine the test agent's ability to regulate transcription of the reporter gene. In instances where identification of antagonists of FK506 induced transcription is desired, the cells are contacted with both FK506 and the test agent. Alkaline phosphatase assays are particularly useful in the practice of the invention because the enzyme is secreted from the cell. Therefore, tissue culture supernatant can be assayed for secreted alkaline phosphatase. In addition, alkaline phosphatase activity can be measured by calorimetric, bioluminescent or chemilumenscent assays such as those described above.

5.5 Immunosuppressive Activity of Test Agents

The present invention relates to the identification of agents capable of modulating hair growth without the side effect of immunosuppression. Thus, in accordance with the invention, any agents identified as possible modulators of hair growth are also tested for their ability to immunosuppress.

Assays designed to measure the immunosuppressive effect of a test agent include, for example, lymphocyte stimulation assays and assays designed to measure cytokine production, i.e., IL-2 production may be performed. One such assay is conducted as follows.

Spleens are excised from euthanized ($CO_2$ asphyxiation) adult male C3H mice ranging in age from seven to sixteen weeks old (live mice commercially available from Harlan Sprague Dawley, Inc., Indianapolis, Ind.). The spleens are placed immediately in cold Hanks Balanced Salt Solution (HBSS, commercially available from Gibco-BRL, Gaithersburg, Md.). The spleens are then ground up between frosted glass slides and filtered through a sterile screen to remove tissue debris. The resulting cell suspension is underlayed with an equal volume of Ficoll-Paque Plus (commercially available from Pharmacia Biotech, Piscataway, N.J.) and centrifuged at 400×g for approximately forty minutes at 20° C. in order to collect the splenocytes. The splenocytes are collected from the interface using a disposable pipet and are washed twice with HBSS, followed by centrifugation at 100×g for ten minutes at 20° C. Splenocytes are resuspended in five to ten mL of cell culture media consisting of phenol red-free RPMI 1640 (culture media commercially available from Gibco-BRL) containing 10% heat-inactivated fetal bovine serum (Gibco-BRL), penicillin (50 U/mL), streptomycin (100 μg/mL), L-glutamine (2 mM), 2-mercaptoethanol ($10^{-5}$ M), and N-2 hydroxyethylpiperazine-N'-2-ethanesulfonic acid (HEPES) (10 mM). The cells are counted and checked for viability using, for example, trypan blue. Splenocytes are resuspended in medium at $10^6$ cells/mL and pipetted into 96 well round bottom plates at $10^5$ cells/well. Splenocytes are activated by addition of 50 μL/well of conconavalin A (final assay concentration=5 μg/ml) in the presence or absence of a test compound. Test compounds are made up as stock solutions in dimethyl sulfoxide (DMSO), then diluted in medium and 50 μL/well added, so that the final concentration of DMSO in the assay is below 0.05%. The plates are incubated at 37° C. with 5% $CO_2$ for 48 hours. The cells are pulsed with 1 μCi/well of methy-$^3$H-thymidine (commercially available from Amersham, Buckinghamshire, England) and incubated an additional 24 hours. The cells are then harvested onto GF/C filter plates (commercially available from Packard, Downers Grove, Ill.), solubilized in Microscint 20 (Packard), and counted on a TopCount microplate scintillation and luminescence plate counter (Packard). Activity is measured as a percentage of control activity in the absence of test compound and plotted versus test compound concentration. The data are fit to a 4-parameter curve fit (Sigmaplot) and $IC_{50}$ values are calculated. As used herein, test compounds are considered non-immunosuppressive if, by using this method, the ratio of (cyclosporin A $IC_{50}$/test compound $IC_{50}$)×100 is less than or equal to 0.02, i.e., as defined herein, a non-immunosuppressive test compound has # 2% of the immunosuppressive activity of cyclosporin A.

Cell viability is assessed using the MTT (3-[4,5-dimethyl-thiazoyl-2-yl]2,5-diphenyl-tetrazolium bromide) dye assay as described by Nelson et al., *J. Immunol.*, 1993, 150(6): 2139–2147, with the exception that the assay is carried out in serum-free, phenol red-free RPMI 1640 and the dye is solubilized in 100 µL/well DMSO and read at an OD of 540 nm with a background correction at 650 nm on a Spectra-Max Plus microplate reader (Molecular Devices, Menlo Park, Calif.).

Alternatively, animal studies can be performed to determine whether a test agent has an immunosuppressive effect.

5.6 Agents that can be Screened in Accordance with the Invention

The assays described above can identify agents that modulate FKBP51/52 activity. For example, agents that affect FKBP51/52 activity include, but are not limited to, agents that bind to FKBP51/52 and modulate the activity of FKBP51/52. Alternatively, agents can be identified that do not bind directly to FKBP51/52, but are capable of altering FKBP51/52 activity by altering the activity of a protein involved in FKBP51/52 signal transduction. Further, agents that affect FKBP51/52 gene activity (by affecting FKBP51/52 gene expression, including molecules, e.g., proteins or small organic molecules, that affect transcription or interfere with splicing events so that expression of the full length or the truncated form of the FKBP51/52 can be modulated) can be identified using the screens of the invention.

The agents which may be screened in accordance with the invention can include, but are not limited to, small organic or inorganic agents, peptides, antibodies and fragments thereof, and other organic agents (e.g., peptidomimetics) that bind to FKBP51/52 and either mimic the activity triggered by any of the known or unknown substrates of FKBP51/52 (i.e., agonists) or inhibit the activity triggered by any of the known or unknown substrates of FKBP51/52 (i.e., antagonists). Agents that bind to FKBP51/52 and either enhance FKBP51/52 activities (i.e., agonists) or inhibit FKBP51/52 activities (i.e., antagonists), will be identified. Agents that bind to proteins that alter/modulate the activity of FKBP51/52 will be identified.

Agents can include, but are not limited to, peptides such as, for example, soluble peptides, such as members of random peptide libraries (see, e.g., Lam, K. S. et al., 1991, *Nature* 354:82–84; Houghten, R. et al., 1991, *Nature* 354: 84–86); and combinatorial chemistry-derived molecular libraries made of D- and/or L-configuration amino acids, phosphopeptides (such as members of random or partially degenerate, directed phosphopeptide libraries); (see, e.g., Songyang, Z. et al., 1993, *Cell* 72:767–778), antibodies (such as polyclonal, monoclonal, humanized, anti-idiotypic, chimeric or single chain antibodies, and FAb, F(ab')$_2$ FV, and FAb expression library fragments, and epitope binding fragments thereof), and small organic or inorganic molecules.

Other agents that can be screened in accordance with the invention include, but are not limited to, small organic molecules that affect the expression of the FKBP51/52 gene or some other gene involved in the FKBP51/52 signal transduction pathway (e.g., by interacting with the regulatory region or transcription factors involved in gene expression); or such agents that affect the activities of the FKBP51/52 or the activity of some other factor involved in modulating FKBP51/52 activity, such as for example, a protein that modifies FKBP51/52 and thereby inactivates FKBP51/52 enzyme activities.

5.7 Compositions Containing Modulators of Hair Growth and Their Uses

The present invention provides methods of modulating hair growth comprising contacting a cell with an effective amount of a FKBP51/52 or CyP40 modulating agent, such as an FKBP51/52 or CyP40 agonist or antagonist identified using the assays as set forth above. An "effective amount" of the FKBP51/52 or CyP40 inhibitor, i.e., antagonist, is an amount that detectably decreases hair growth. An "effective amount" of the FKBP51/52 or CyP40 activator, i.e., agonist, is an amount that detectably increases hair growth.

The present invention further provides methods of modulating hair growth in a subject in need of such treatment, comprising administering to the subject an effective amount of an agent that modulates FKBP51/52 or CyP40 activity identified as set forth above.

The present invention further provides compositions comprising one or more activators or inhibitors of FKBP51/52 and CyP40 activity. The composition may act directly on FKBP51/52 or CyP40, or alternatively may act on proteins involved in the FKBP51/52 and CyP40 signal transduction pathway.

The present invention further provides pharmaceutical compositions comprising an effective amount of an agent capable of modulating the activity of FKBP51/52, CyP40-, or FKBP51/52, CyP40-mediated signal transduction and/or the expression of FKBP51/52 or CyP40, thereby regulating hair growth, and a pharmaceutically acceptable carrier. In a specific embodiment, the term "pharmaceutically acceptable" means approved by a regulatory agency of the federal or a state government or listed in the U.S. Pharmacopeia or other generally recognized pharmacopoeia for use in animals, and more particularly in humans. The term "carrier" refers to a diluent, adjuvant, excipient, or vehicle with which the therapeutic is administered. Examples of suitable pharmaceutical carriers are described in *Remington: The Science and Practice of Pharmacy*, Gennaro et al. (eds), 20$^{th}$ Edition, Lippincott Williams & Wilkins, Philadelphia, Pa. (ISBN 0-683-306472).

The invention further provides for the treatment of various disorders associated with hair growth by administration of an agent that regulates the expression or activity of FKBP51/52 or CyP40. Such agents include, but are not limited to, FKBP51/52 or CyP40 agonists and antagonists. Such disorders include, but are not limited to, male pattern baldness, female pattern baldness, toxic baldness, alopecia greata and scarring alopecia. In addition, the agent can be used to treat subjects with hair loss associated with exposure to radiation or chemotherapy.

The agents of the invention are preferably tested in vitro, and then in vivo in an animal system for a desired therapeutic or prophylactic activity, prior to testing and use in humans. For example, in vitro assays that can be used to determine whether administration of a specific therapeutic is indicated include in vitro cell culture assays in which cells expressing FKBP51/52 or CyP40 are exposed to or otherwise administered a therapeutic agent, where the effect of such a therapeutic agent on FKBP51/52 or CyP40 is then observed upon FKBP51/52 or CyP40 activity is then observed. In a specific embodiment of the invention the ability of an agent to regulate the signal transduction pathway mediated by CyP40 or FKBP51/52 is assayed.

The invention provides methods of treatment and/or prophylaxis comprising administering to a subject in need thereof an effective amount of a hair growth modulating agent of the invention. In a preferred aspect, the agent is substantially purified. The subject is preferably an animal, more preferably a mammal, and most preferably a human.

Various delivery systems are known and can be used to administer an agent capable of regulating hair growth, e.g., encapsulation in liposomes, microparticles, microcapsules. Methods of introduction include, but are not limited to, intradermal, topical, intramuscular, intraperitoneal, intravenous, subcutaneous, intranasal, epidural, and oral routes. The agents may be administered by any convenient route, for example, by infusion or bolus injection, by absorption through epithelial or mucocutaneous linings (e.g., oral mucosa, rectal and intestinal mucosa, etc.), and may be administered together with other biologically active agents. Administration can be systemic or local, and is preferably adopted for topical applications.

In a specific embodiment, it may be desirable to administer the compositions of the invention locally to a specific area of the body. This may be achieved, for example, and not by way of limitation, by topical application. The active compounds identified according to the methods of the present invention are generally administered in the form of pharmaceutical compositions comprising at least one of such compounds together with a pharmaceutically acceptable vehicle or diluent. Such compositions are generally formulated in a conventional manner utilizing solid or liquid vehicles or diluents as appropriate for topical administration, in the form of solutions, oils, gels, creams, jellies, pastes, lotions, ointments, salves, leave-on and rinse-out hair conditioners, shampoos, aerosols and the like.

Examples of vehicles for application of an active compound identified according to a method of the present invention include an aqueous or water-alcohol solution, an emulsion of the oil-in-water or water-in-oil type, an emulsified gel, or a two-phase system. Preferably, the compositions according to the invention are in the form of lotions, creams, milks, gels, masks, microspheres or nanospheres, or vesicular dispersions. In the case of vesicular dispersions, the lipids of which the vesicles are made can be of the ionic or nonionic type, or a mixture thereof.

Topical compositions containing the active compound can be admixed with a variety of carrier materials well known in the art, such as, for example, water alcohols, aloe vera gel, allantoin, glycerin, vitamin A and E oils, mineral oil, propylene glycol, PPG-2 myristyle propionate, and the like, as well as any of various types of penetration enhancers, viscosity enhancing agents, pH stabilizers, anti-oxidants, preservatives, perfumes, coloring agents, etc.

Other materials suitable for use in topical carriers include, for example, emollients, solvents, humectants, thickeners and powers, as known in the art.

The compositions of the present invention may also optionally comprise other hair growth modulating agents such as potassium channel openers, anti-androgens, thyroid hormones and derivatives and analogs thereof, prostaglandin agonists or antagonists, retinoids, triterpenes, and others known in the art or to be identified.

The amount of the agent of the invention which will be effective in the treatment of a particular disorder will depend on the nature of the disorder and can be determined by standard clinical techniques. In vitro assays may optionally be employed to help identify optimal dosage ranges. The precise dose to be employed in the formulation will depend on the route of administration and the nature of the disorder, and should be decided according to the judgment of the medical practitioner and in view of each patient's circumstances. Effective doses can be extrapolated from dose response curves derived from in vitro or animal model test systems.

The invention also provides a pharmaceutical pack or kit comprising one or more containers comprising one or more of the ingredients of the pharmaceutical compositions of the invention. Optionally associated with such container(s) can be a notice in a form prescribed by a governmental agency regulating the manufacture, use or sale of pharmaceuticals or biological products, which notice reflects approval by the agency of manufacture, use or sale for human administration. The kit may further comprise printed instructions or a printed label directing the use of the composition to modulate, i.e., to stimulate or inhibit, hair growth.

The following examples illustrate the preferred modes of making and practicing the present invention but are not meant to limit the scope of the invention since alternative methods may be utilized to obtain similar

6. EXAMPLE

FKBP51/52 Mediated Hair Growth

The examples presented below demonstrate that (i) FKBP51 and FKBP52 are selectively expressed in dermal papillae; (ii) FKBP51/52 co-precipitate with hsp90, AFX-1 Gli3 and the hairless protein; and (iii) expression of the BMP4 and HNF3β gene, a Gli3 responsive gene is activated by FK506.

6.1 Materials and Methods 6.1.1 Reverse Transcription

A commercial RT-PCR kit (Promega Access RT-PCR kit) was used for detection of FKBP51, FKBP52, and CyP40 mRNA in different human cells. The sequence of primers used for human FKBP51 is: TGAAGAAAGCCCCACAGC (SEQ ID NO:1) (forward primer) and CTCCAAAAC-CATATCTTGGTCC (SEQ ID NO:2) (reverse primers). Primer sequence for human FKBP52 is: ACATTGCCAT-AGCCACCA (SEQ ID NO:3) (forward primer) and AGC-CAAGACACGATCTTC (SEQ ID NO:4) (reverse primer). Primer sequence for human CyP40 is: TGAAGGAAG-GAGATGACGGG (SEQ ID NO:5) (forward primer) and TCCTCAGGGAAATCTGGATGA (SEQ ID NO:6) (reverse primer).

Total RNA was extracted from cultured cells using TRI-ZOL reagent (Life Technologies) according to manufacturer's instruction. The RNA was treated with DNase to remove potential contamination by genomic DNA and then used in RT-PCR reaction. The PCR reaction product was run on a 2% agarose gel to visualize the amplified product and digested with appropriate restriction enzymes to confirm the products.

6.1.2 Tissue Extraction

Human skin tissue was extracted using TPER reagent (Pierce, Rockford, Ill.) at a ratio of 10:1 (extraction buffer: tissue; vol:wt) on ice using a Polytron homogenizer in the presence of protease inhibitors (Protease Inhibitor Cocktail, 1:50 dilution; Sigma, St. Louis, Mo.) to form a lysate.

6.1.3 Coupling of Antibodies to Magnetic Resin Protein G Sepharose

Antibodies used included anti-hsp90 (monoclonal IgG1 with 1 mg/ml BSA; TL) and anti-FKBP52 (anti-peptide polyclonal N17 and C19 Abs; Santa Cruz Biotechnologies). Antibodies were concentrated and washed 3× with PBS using Amicon Microcon-30. Antibodies were coupled to tosyl-activated Dyna M-450 beads in neutral pH PBS buffer overnight at 37° C. Resins were blocked with Tris-HCl, pH 8 for 4 hours, 37° C.

6.1.4 Immunoprecipitation

FK506 was added to the lysate to a final concentration of 1 µM. Antibody complexes were immunoprecipitated in TPER buffer at 6° C. overnight. Complexes were washed 10× with Tris/saline (4° C.) and sequentially eluted with 1M $NH_4CO_3$ or 20 mM Tris, pH 7.4, 0.3 M NaCl: (5×100 µl) and 0.1% TFA, 5% MeOH (5×100 µl). Complexes were concentrated and buffer was exchanged (mw 3500) for salt elutions or reduced in volume under vacuum for TFA/MeOH elutions. Samples were stored at −20° C.

6.1.5 Protease Digestion

Proteins were suspended in 1 M GnHCl, 100 mM $NH_4CO_3$, 0.5 mM DTT and subject to digestion with trypsin (Promega) or gluC (Roche) for about 18 hours at 37° C. Digests were desalted using C18 ZipTips (Millipore) eluted with 60% acetonitrile, 0.1% TFA.

6.1.6 Mass Spectrometry Analysis

The peptide digests were analyzed by matrix-assisted laser disorption ionization (MALDI) time of flight (TOF) spectrometry. Essentially, peptides were mixed with matrix (1:1 sample: α-cyano-4-hydroxycinnamic acid; 20 mg/ml-HCCA, 30% acetonitrile, 0.1% TFA) in which the dried droplet method was used. Peptides were analyzed using a Voyager DE-Pro spectrometer (PE BioSystems) in reflector mode (2 m flight length) with a positive ion accelerating voltage of 20 kV, a grid voltage of 12.8 kV, guide wire voltage of 1400 V, using 100 ns delayed extraction. Greater than 64 scans were averaged per spectra. 30–50 fmols each of bradykinin and ACTH (amino acid residues 18–39) were used as internal mass standards.

6.1.7 Database Searching

Peptide spectra were compared using ProFound [http://nt2/prowl/prowl.html] or RADARS(OSI internal). Mass error tolerance was typically 30 ppm. One missed cleavage was allowed. Modifications were not initially considered. Both SWISSPROT and GENBANK NR databases were searched.

Figure 3A:
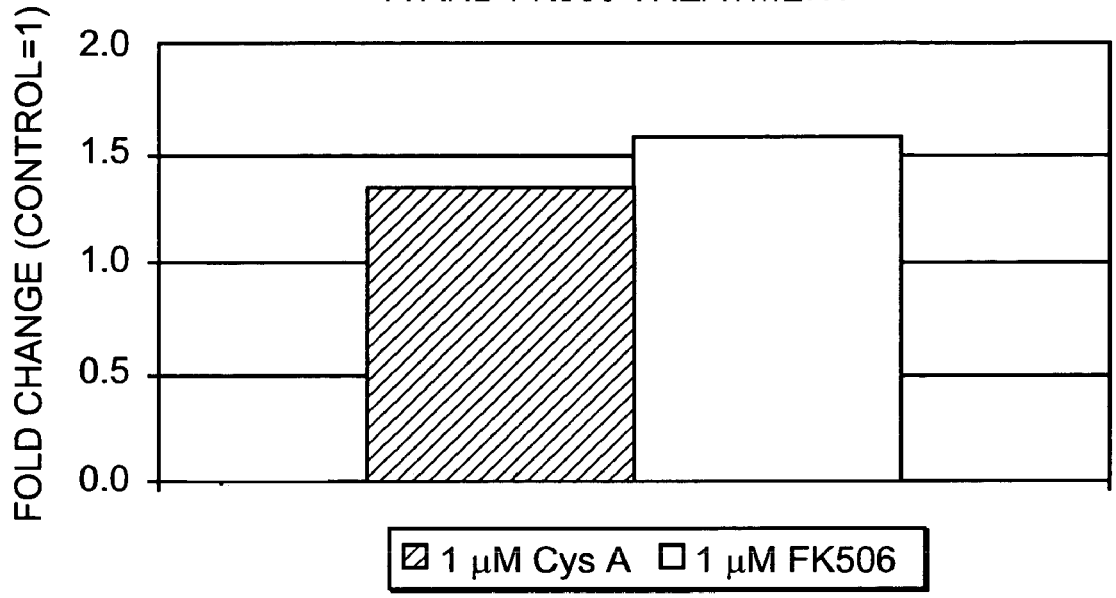
FIG. 3A is a graphic representation demonstrating stimulation of BMP4 transcription four days after FK506 and cyclosporin A treatment.
Figure 3B:
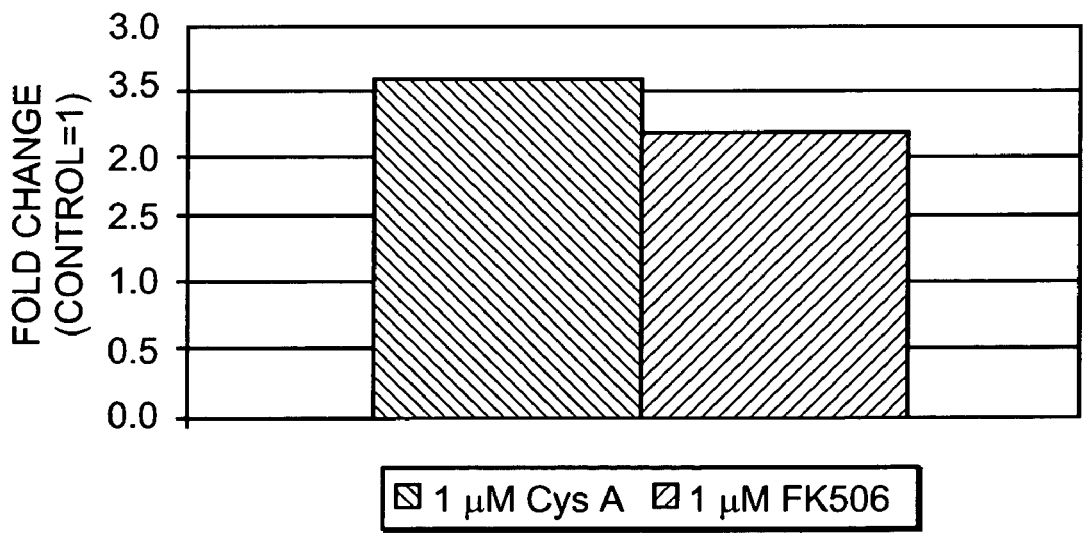
FIG. 3B is a graphic representation demonstrating stimulation of HNF3β transcription four days after FK506 and cyclosporin A treatment.

6.1.8 Induction of BMP4 and HNF3β mRNA by Cyclosporin A and FK506 Treatment Primary human dermal fibroblasts (for detectin of BMP4) and skin keratinocytes (for detection of HNF3β) were cultured and treated with 1 uM of cyclosporin A or FK506. Total RNA was harvested at days 2 and 4 of treatment. Real time PCR was used to quantify the BMP4 and HNF3β mRNA level. ABI PRISM 7700 sequence detector, TaqMan PCR kit, and PCR primers designed with commercial software labeled with fluorescence dyes were used for RNA quantification. The results as presented in FIG. 3 show that cyclosporin A and FK506 both up-regulate the level of BMP4 and HNF3β mRNA.

In addition, downstream target genes of Gli3 were found to be up regulated by cyclosporin A and FK506 treatment in skin cells such as dermal fibroblasts and skin keratinocytes. As indicated in FIG. 3, BMP4 and HNF3β mRNA level were induced by cyclosporin A or FK506 treatment.

6.1.9 Induction of Thyroid Hormone Receptor (TR) Mediated Transcription by Fk506 and Cyclosporin A Four tandem thyroid hormone response elements (TRE) (AGGTCA CAGG AGGTCA) (underlined sequence is repeated) (SEQ ID NO:7) were synthesized in a single oligonucleotide and ligated 5' of thymidine kinase (TK) promoter using standard procedures. A plasmid (TRE-TK/ pUV120puro) was constructed by linking the resulting TRE/ TK promoter 5' of the luciferase reporter gene from *H.* *pyralis*, de Wet Jr. et al, 1986, *Methods Enzymol* 133:3–14, together with a gene encoding a protein conferring resistance to the antibiotic puromycin expressed under the control of the SV40 promoter. In this plasmid the expression of the luciferase gene is under the direct control of the TRE-TK promoter and is inducible by agonists of the thyroid hormone nuclear receptor (TR). HeLa cells (ATCC, Manassas, Va. 20108, #CCL-2) were transfected with plasmid DNA by electroporation using standard procedures, and drug resistant cell lines were selected using puromycin Signa-Aldrich Corp., St. Louis, Mich. Drug resistant cell lines (HeLa/TRE) were selected for responsiveness to thyroid hormone, and a single, stably transfected, clonal line was used in subsequent experiments.

Mass spectrometry experiments indicated that hair growth was likely mediated by a protein complex comprising in part hsp90, either cyclophillin 40, FKBP 51 or 52, the zinc finger transcription factor hairless, and a nuclear hormone receptor (thyroid hormone receptor, androgen receptor, vitamin D receptor or glucocorticoid receptor).

In order to establish the role of the thyroid hormone nuclear receptor in immunophillin signaling, cyclosporine A, FK506 and thyroid hormone T3 were evaluated for their ability to increase thyroid hormone nuclear receptor signaling. HeLa/TRE cells were seeded at a density of 10,000 cells per well in 96 well microtiter plates in DMEM culture media containing 1% charcoal stripped FCS, 2 mM glutamine and antibiotics (penicillin and streptomycin). The cells were treated with increasing concentrations (20 nM, 2 nM, 200 pM, and 20 pM) of cyclosporin A or FK506) Sigma-Aldrich Corp., St. Louis, Mich.; (Calbiochem-Nova biocheryl Corp., San Diego, Calif.) for 16 hours and the activity of the luciferase reporter gene was measured) de Wet Jr. et al, 1986, *Methods Enzymol* 133:3–14.

6.2 Results

Dermal Papillar (DP) cells are critical for hair growth. In cultured human dermal papillar cells, CyP40 and FKBP51/ 52 were detected using RT-PCR (FIG. 2). The levels of FKBP51/52 are much greater than those of FKBP 12/13. The levels of FKBP12/13, which mediate the immunosuppressive effect of FK506, was close to the detection limit, indicating that their levels of expression were very low. The expression patterns in human dermal fibroblasts and keratinocytes have also been studied and were found to be identical.

Mass spectrometry analysis of hsp90 and FKBP52 immunoprecipitated complexes derived from human scalp skin reveal the presence of three transcription factors. The factors include the zinc finger protein hairless, the sonic hedgehog stimulated factor Gli-3, and AFX-1.

Data also suggest that in human skin FK506 might alter hairless interaction with hsp90 protein complexes. Hairless may then translocate to the nucleus and stimulate transcription of genes regulating hair growth.

In addition, downstream target genes of Gli3 such as BMP4 and HNF3 were found to be upregulated by FK506 treatment (FIG. 3).

Hsp90 and FKBP52 complexes relevant to immunophillin action were identified from human scalp skin extracts using monoclonal antibodies, protease digestion, mass spectrometric measurement of peptide masses and protein database searching. The following proteins were identified from trypsin and/or GluC digests subject to mass spectrometric analysis:

TABLE 1

Anti-hsp90 and anti-FKBP52
human skin extract + FK506
30 ppm (SWISSPROT)

|  | Trypsin | GluC |
|---|---|---|
| Protein folding, immunophilins, stress-response | | |
| hsp90-beta | x | x |
| hsp90-alpha | x | x |
| hsp70s | x | x |
| FKBP-51 | x | x |
| hsp27 | x | x |
| FKBP-52 | x | x |
| FRAP | x | x |
| hsp110 | x | x |
| hsp40 protein-3 (DNAJ homolog 1) | x | x |
| prolyl 4-hydroxylase (alpha and beta subunits) | x | |
| protein disulfide isomerases | x | x |
| osmotic stress protein 94 (hsp70 related) | x | x |
| cyclophilin 40 | x | |
| Steroid-like receptors | | |
| estrogen receptors | x | x |
| glucocorticoid receptor | x | x |
| androgen receptor | x | |
| RXR-beta | | x |
| TRIP-12 | | x |
| thyroid hormone receptor | x | x |
| Protein degradation | | |
| cullin-2 | x | x |
| cullin-3 | x | x |
| ubiquitin carboxy terminal hydrolases | x | x |
| 26S proteosome subunits | x | x |
| ubiquitin activating enzyme E1 | | x |
| Transcription and chromatin remodeling | | |
| human hairless (zfp) | x | x |
| heat shock factor protein-2 (HSF-2) | x | |
| GLI-3 | x | x |
| AFX1 putative whn factor (forkhead domain) | x | |

Figure 4:
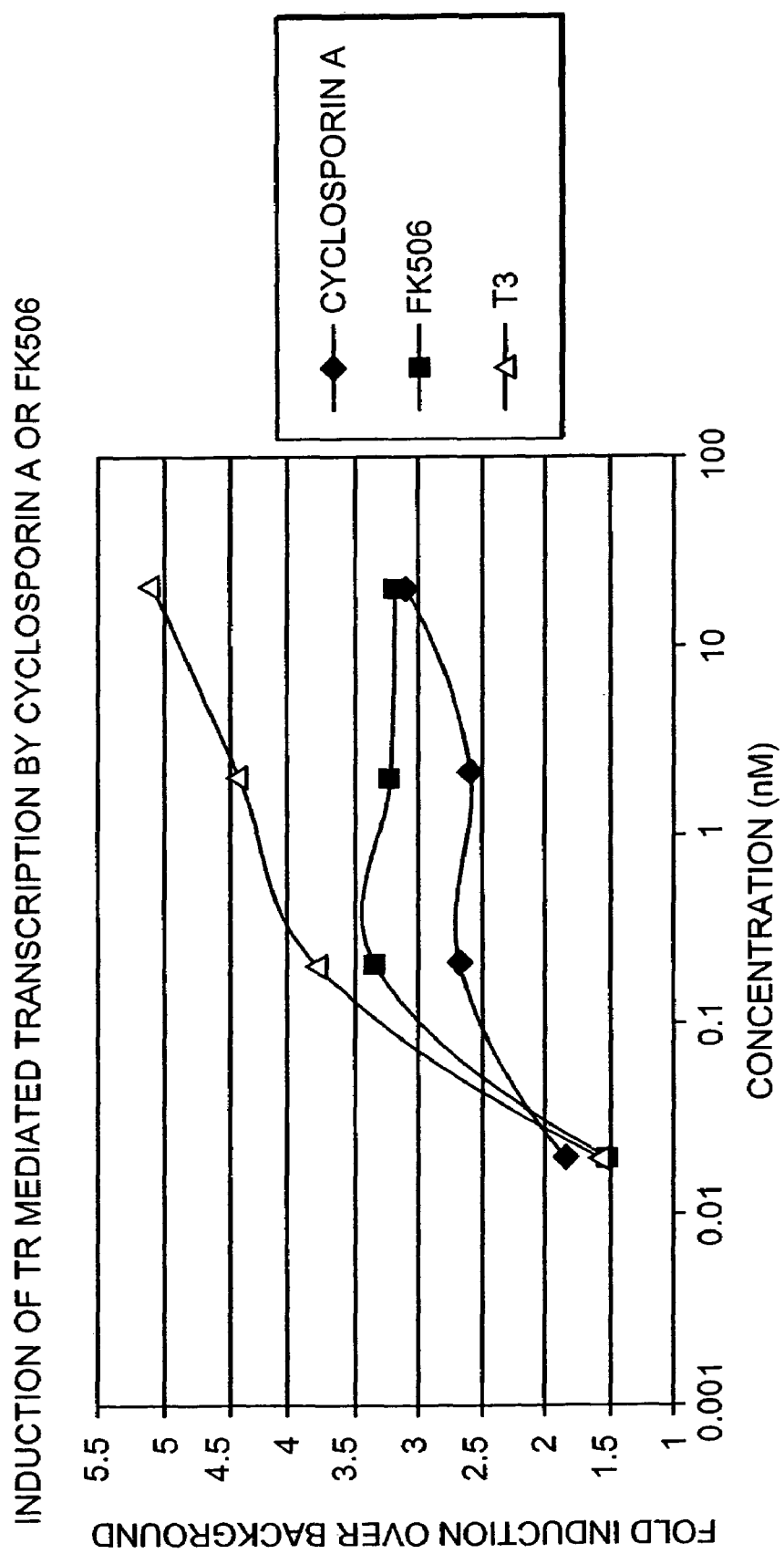
FIG. 4 is a graphic presentation of the induction of TR mediated transcription by cyclosporin A or FK506.

The data show that cyclosporin A or FK506 induces thyroid hormone receptor mediated transcription in a dose dependent manner (FIG. 4). Binding of ligand to cyclophilin 40 (cyclosporin A) or FKBP51/52 (FK506) proteins in the hsp90 complex clearly activates the transcriptional activity of thyroid hormone receptor. The hairless protein, an accessory protein of thyroid hormone receptor, also can modulate cyclosporin A or FK506 action and thereby regulate hair growth.

Equivalents

The present invention is not to be limited in scope by the specific embodiments described herein which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Various publications are cited herein, the contents of which are hereby incorporated, by reference, in their entireties.

We claim:

1. A method for identifying a compound that modulates interactions between FKBP51, hsp90, and a binding partner selected from the group consisting of hairless, AFX-1, gli3, and a combination thereof, comprising:
   (i) contacting a cell that expresses, or a preparation comprising FKBP51, hsp90, and the binding partner with a test compound;
   (ii) determining the level of complex formation between FKBP51, hsp90, and the binding partner in the cell or the preparation contacted with the test compound; and
   (iii) comparing the level of complex formation obtained in (ii) to the level of complex formation between FKBP51, hsp90, and the binding partner in the cell or the preparation in the absence of the test compound;
   wherein a difference in the level of complex formation in the presence versus in the absence of the test compound indicates that the test compound is capable of modulating interactions between FKBP51 hsp90, and the binding partner.

2. The method of claim 1, wherein the level of complex formation is detected using an immunoassay.

3. The method of claim 1, further comprising the step of determining whether the test compound has immunosuppressive activity.

4. The method of claim 1, wherein the test compound increases interactions between FKBP51, hsp90, and the binding partner.

5. The method of claim 1, wherein the test compound decreases interactions between FKBP51, hsp90, and the binding partner.

6. A method for identifying a compound that inhibits complex formation between a hairless gene product and a binding partner selected from the group consisting of FKBP51, FKBP52, CyP40, a nuclear hormone receptor wherein the nuclear receptor is not a thyroid hormone receptor, hsp90, and a combination thereof, comprising:
   (i) contacting a cell that expresses or a preparation comprising the hairless gene product and the binding partner with a test compound;

(ii) determining the level of complex formation between the hairless gene product and the binding partner in the cell or the preparation contacted with the test compound; and (iii) comparing the level of complex formation obtained in (ii) to the level of complex formation between the hairless gene product and the binding partner in the cell or the preparation in the absence of the test compound:

wherein a decrease in the level of complex formation in the presence versus in the absence of the test compound indicates that the test compound is capable of inhibiting interactions between the hairless gone product and the binding partner.

7. The method of claim 6, further comprising the step of determining whether the test compound has immunosuppressive activity.

8. The method of claim 6, further comprising determining whether the test compound binds to the hairless gene product.

9. The method of claim 6, wherein the level of complex formation is detected using an immunoassay.

10. A method for identifying a compound that inhibits complex formation between an AFX-1 gene product and a binding partner selected from the group consisting of FKBP51, FKBP52, CyP40, a nuclear hormone receptor, hsp90, and a combination thereof, comprising:

(i) contacting a cell that expresses, or a preparation comprising the AFX-1 gene product and the binding partner with a test compound;

(ii) determining the level of complex formation between the AFX-1 gene product and the binding partner in the cell or the preparation contacted with the test compound; and (iii) comparing the level of complex formation obtained in (ii) to the level of complex formation between the AFX-1 gene product and the binding partner in the cell or the preparation in the absence of the test compound;

wherein a decrease in the level of complex formation in the presence versus in the absence of the test compound indicates that the test compound is capable of inhibiting interactions between the AFX-1 gene product and the binding partner.

11. The method of claim 10, further comprising the step of determining whether the test compound has immunosuppressive activity.

12. The method of claim 10, further comprising determining whether the test compound binds to the AFX-1 gene product.

13. The method of claim 10, wherein the level of complex formation is detected using an immunoassay.

14. A method for identifying a compound that inhibits complex formation between a gli3 gene product and a binding partner, selected from the group consisting of FKBP51, FKBP52, CyP40, a nuclear hormone receptor, hsp90, and a combination thereof, comprising:

(i) contacting a cell that expresses, or a preparation comprising the gli3 gene product and the binding partner with a test compound;

(ii) determining the level of complex formation between the gli3 gene product and the binding partner in the cell or the preparation contacted with the test compound; and (iii) comparing the level of complex formation obtained in (ii) to the level of complex formation between the gli3 gene product and the binding partner in the cell or the preparation in the absence of the test compound;

wherein a decrease in the level of complex formation in the presence versus in the absence of the test compound indicates that the test compound is capable of inhibiting interactions between the gli3 gene product and the binding partner.

15. The method of claim 14, further comprising the step of determining whether the test compound has immunosuppressive activity.

16. The method of claim 14, further comprising determining whether the test compound binds to the gli3 gene product.

17. The method of claim 14, wherein the level of complex formation is detected using an immunoassay.

18. A method for identifying a compound that increases complex formation between a hairless gene product, an AFX-1 gene product, or a gli3 gene product, and a binding partner selected from the group consisting of FKBP51, FKBP52, CyP40, a nuclear hormone receptor wherein the nuclear receptor is not a thyroid hormone receptor, hsp90, and a combination thereof, comprising:

(i) contacting a cell that expresses, or a preparation comprising the hairless gene product, the AFX-1 gene product, or the gli3 gene product, and the binding partner, with a test compound;

(ii) determining the level of complex formation between the hairless gene product, the AFX-1 gene product, or the gli3 gene product, and the binding partner in the cell or the preparation contacted with the test compound; and (iii) comparing the level of complex formation obtained in (ii) to the level of complex formation between the hairless gene product the AFX-1 gene product, or the gli3 gene product, and the binding partner in the cell or the preparation in the absence of the test compound;

wherein an increase in the level of complex formation in the presence versus in the absence of the test compound indicates that the test compound is capable of increasing interactions between the hairless gene product, the AFX-1 gene product, or the gli3 gene product, and the binding partner.

19. The method of claim 18, further comprising determining whether the test compound binds to the hairless gene product, the AFX-1 gene product, or the gli3 gene product.

20. The method of claim 18, further comprising the step of determining whether the test compound has immunosuppressive activity.

21. The method of claim 18, wherein the level of complex formation is detected using an immunoassay.

22. A method for identifying a compound that modulates interactions between FKBP52, hsp90, and a binding partner selected from the group consisting of hairless, AFX-1, gli3, and a combination thereof, comprising:

(i) contacting a cell that expresses, or a preparation comprising FKBP52, hsp90, and the binding partner with a test compound;

(ii) determining the level of complex formation between FKBP52, hsp90, and the binding partner in the cell or the preparation contacted with the test compound; and (iii) comparing the level of complex formation obtained in (ii) to the level of complex formation between FKBP52, hsp90, and the binding partner in the cell or the preparation in the absence of the test compound;

wherein a difference in the level of complex formation in the presence versus in the absence of the test compound indicates that the test compound is capable of modulating interactions between FKBP52, hsp90, and the binding partner.

23. The method of claim 22, wherein the level of complex formation is detected using an immunoassay.

24. The method of claim 22, further comprising the step of determining whether the test compound has immunosuppressive activity.

25. The method of claim 22, wherein the test compound increases interactions between FKBP52, hsp90, and the binding partner.

26. The method of claim 22, wherein the test compound decreases interactions between FKBP52, hsp90, and the binding partner.

27. A method for identifying a compound that modulates interactions between Cyp40, hsp90, and a binding partner selected from the group consisting of hairless, AFX-1, gli3, and a combination thereof, comprising:
   (1) contacting a cell that expresses, or a preparation comprising Cyp40, hsp90, and the binding partner with a test compound;
   (ii) determining the level of complex formation between Cyp40, hsp90, and the binding partner in the cell or the preparation contacted with the test compound; and
   (iii) comparing the level of complex formation obtained in (ii) to the level of complex formation between Cyp40, hsp90, and the binding partner in the cell or the preparation in the absence of the test compound;
   wherein a difference in the level of complex formation in the presence versus in the absence of the test compound indicates that the test compound is capable of modulating interactions between Cyp40, hsp90, and the binding partner.

28. The method of claim 27, wherein the level of complex formation is detected using an immunoassay.

29. The method of claim 27, further comprising the step of determining whether the test compound has immunosuppressive activity.

30. The method of claim 27, wherein the test compound increases interactions between Cyp40, hsp90, and the binding partner.

31. The method of claim 27, wherein the test compound decreases interactions between Cyp40, hsp90, and the binding partner.

32. A method for identifying a compound that modulates interactions between FKBP51 and a binding partner selected from the group consisting of hairless, AFX-1, gli3, hsp90, and a combination thereof, comprising:
   (i) contacting a cell that expresses, or a preparation comprising FKBP51, and the binding partner with a test compound;
   (ii) determining the level of complex formation between FKBP51 and the binding partner in the cell or the preparation contacted with the test compound; and
   (iii) comparing the level of complex formation obtained in (ii) to the level of complex formation between FKBP51 and the binding partner in the cell or the preparation in the absence of the test compound;
   wherein a difference in the level of complex formation in the presence versus in the absence of the test compound indicates that the test compound is capable of modulating interactions between FKBP51 and the binding partner.

33. The method of claim 32, wherein the level of complex formation is detected using an immunoassay.

34. The method of claim 32, further comprising the step of determining whether the test compound has immunosuppressive activity.

35. The method of claim 32, wherein the test compound increases interactions between FKBP51 and the binding partner.

36. The method of claim 32, wherein the test compound decreases interactions between FKBP51 and the binding partner.

37. A method for identifying a compound that modulates interactions between FKBP52 and a binding partner selected from the group consisting of hairless, AFX-1, gli3, hsp90, and a combination thereof, comprising:
   (i) contacting a cell that expresses, or a preparation comprising FKBP52, and the binding partner with a test compound;
   (ii) determining the level of complex formation between FKBP52 and the binding partner in the cell or the preparation contacted with the test compound; and
   (iii) comparing the level of complex formation obtained in (ii) to the level of complex formation between FKBP52 and the binding partner in the cell or the preparation in the absence of the test compound;
   wherein a difference in the level of complex formation in the presence versus in the absence of the test compound indicates that the test compound is capable of modulating interactions between FKBP52 and the binding partner.

38. The method of claim 37, wherein the level of complex formation is detected using an immunoassay.

39. The method of claim 37, further comprising the step of determining whether the test compound has immunosuppressive activity.

40. The method of claim 37, wherein the test compound increases interactions between FKBP52 and the binding partner.

41. The method of claim 37, wherein the test compound decreases interactions between FKBP52 and the binding partner.

42. A method for identifying a compound that modulates interactions between Cyp40 and a binding partner selected from the group consisting of hairless, AFX-1, gli3, hsp90, and a combination thereof, comprising:
   (i) contacting a cell that expresses, or a preparation comprising Cyp40, and the binding partner with a test compound;
   (ii) determining the level of complex formation between Cyp40 and the binding partner in the cell or the preparation contacted with the test compound; and
   (iii) comparing the level of complex formation obtained in (ii) to the level of complex formation between Cyp40 and the binding partner in the cell or the preparation in the absence of the test compound;
   wherein a difference in the level of complex formation in the presence versus in the absence of the test compound indicates that the test compound is capable of modulating interactions between Cyp40 and the binding partner.

43. The method of claim 42, wherein the level of complex formation is detected using an immunoassay.

44. The method of claim 42, further comprising the step of determining whether the test compound has immunosuppressive activity.

45. The method of claim 42, wherein the test compound increases interactions between Cyp40 and the binding partner.

46. The method of claim 42, wherein the test compound decreases interactions between Cyp40 and the binding partner.

* * * * *

SEQUENCE LISTING

```
<160> NUMBER OF SEQ ID NOS: 21

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgaagaaagc cccacagc                                                 18

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctccaaaacc atatcttggt cc                                            22

<210> SEQ ID NO 3
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
acattgccat agccacca                                                        18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agccaagaca cgatcttc                                                        18

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgaaggaagg agatgacggg                                                      20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcctcaggga aatctggatg a                                                    21

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aggtcacagg aggtca                                                          16

<210> SEQ ID NO 8
<211> LENGTH: 457
<212> TYPE: PRT
<213> ORGANISM: Homo sapiens

<400> SEQUENCE: 8

Met Thr Thr Asp Glu Gly Ala Lys Asn Asn Glu Glu Ser Pro Thr Ala
  1               5                  10                  15

Thr Val Ala Glu Gln Gly Glu Asp Ile Thr Ser Lys Lys Asp Arg Gly
                 20                  25                  30

Val Leu Lys Ile Val Lys Arg Val Gly Asn Gly Glu Glu Thr Pro Met
             35                  40                  45
```

-continued

```
Ile Gly Asp Lys Val Tyr Val His Tyr Lys Gly Lys Leu Ser Asn Gly
         50                  55                  60

Lys Lys Phe Asp Ser Ser His Asp Arg Asn Glu Pro Phe Val Phe Ser
 65                  70                  75                  80

Leu Gly Lys Gly Gln Val Ile Lys Ala Trp Asp Ile Gly Val Ala Thr
                 85                  90                  95

Met Lys Lys Gly Glu Ile Cys His Leu Leu Cys Lys Pro Glu Tyr Ala
                100                 105                 110

Tyr Gly Ser Ala Gly Ser Leu Pro Lys Ile Pro Ser Asn Ala Thr Leu
            115                 120                 125

Phe Phe Glu Ile Glu Leu Leu Asp Phe Lys Gly Glu Asp Leu Phe Glu
    130                 135                 140

Asp Gly Gly Ile Ile Arg Arg Thr Lys Arg Lys Gly Glu Gly Tyr Ser
145                 150                 155                 160

Asn Pro Asn Glu Gly Ala Thr Val Glu Ile His Leu Glu Gly Arg Cys
                165                 170                 175

Gly Gly Arg Met Phe Asp Cys Arg Asp Val Ala Phe Thr Val Gly Glu
            180                 185                 190

Gly Glu Asp His Asp Ile Pro Ile Gly Ile Asp Lys Ala Leu Glu Lys
        195                 200                 205

Met Gln Arg Glu Glu Gln Cys Ile Leu Tyr Leu Gly Pro Arg Tyr Gly
    210                 215                 220

Phe Gly Glu Ala Gly Lys Pro Lys Phe Gly Ile Glu Pro Asn Ala Glu
225                 230                 235                 240

Leu Ile Tyr Glu Val Thr Leu Lys Ser Phe Glu Lys Ala Lys Glu Ser
                245                 250                 255

Trp Glu Met Asp Thr Lys Glu Lys Leu Glu Gln Ala Ala Ile Val Lys
            260                 265                 270

Glu Lys Gly Thr Val Tyr Phe Lys Gly Gly Lys Tyr Met Gln Ala Val
        275                 280                 285

Ile Gln Tyr Gly Lys Ile Val Ser Trp Leu Glu Met Glu Tyr Gly Leu
    290                 295                 300

Ser Glu Lys Glu Ser Lys Ala Ser Glu Ser Phe Leu Leu Ala Ala Phe
305                 310                 315                 320

Leu Asn Leu Ala Met Cys Tyr Leu Lys Leu Arg Glu Tyr Thr Lys Ala
                325                 330                 335

Val Glu Cys Cys Asp Lys Ala Leu Gly Leu Asp Ser Ala Asn Glu Lys
            340                 345                 350

Gly Leu Tyr Arg Arg Gly Glu Ala Gln Leu Leu Met Asn Glu Phe Glu
        355                 360                 365

Ser Ala Lys Gly Asp Phe Glu Lys Val Leu Glu Val Asn Pro Gln Asn
    370                 375                 380

Lys Ala Ala Arg Leu Gln Ile Ser Met Cys Gln Lys Lys Ala Lys Glu
385                 390                 395                 400

His Asn Glu Arg Asp Arg Arg Ile Tyr Ala Asn Met Phe Lys Lys Phe
                405                 410                 415

Ala Glu Gln Asp Ala Lys Glu Glu Ala Asn Lys Ala Met Gly Lys Lys
            420                 425                 430

Thr Ser Glu Gly Val Thr Asn Glu Lys Gly Thr Asp Ser Gln Ala Met
        435                 440                 445

Glu Glu Glu Lys Pro Glu Gly His Val
    450                 455
```

<210> SEQ ID NO 9
<211> LENGTH: 1694
<212> TYPE: DNA
<213> ORGANISM: Homo sapiens

<400> SEQUENCE: 9

```
gggccggctc gcgggcgctg ccagtctcgg gcggcggtgt ccggcgcgcg ggcggcctgc      60
tgggcgggct gaagggttag cggagcacgg gcaaggcgga gagtgacgga gtcggcgagc     120
ccccgcggcg acaggttctc tacttaaaag acaatgacta ctgatgaagg tgccaagaac     180
aatgaagaaa gccccacagc cactgttgct gagcagggag aggatattac ctccaaaaaa     240
gacaggggag tattaaagat tgtcaaaaga gtggggaatg gtgaggaaac gccgatgatt     300
ggagacaaag tttatgtcca ttacaaagga aaattgtcaa atggaaagaa gtttgattcc     360
agtcatgata gaaatgaacc atttgtcttt agtcttggca aaggccaagt catcaaggca     420
tgggacattg gggtggctac catgaagaaa ggagagatat gccatttact gtgcaaacca     480
gaatatgcat atggctcggc tggcagtctc cctaaaattc cctcgaatgc aactctcttt     540
tttgagattg agctccttga tttcaaagga gaggatttat ttgaagatgg aggcattatc     600
cggagaacca aacggaaagg agagggatat tcaaatccaa acgaaggagc aacagtagaa     660
atccacctgg aaggccgctg tggtggaagg atgtttgact gcagagatgt ggcattcact     720
gtgggcgaag gagaagacca cgacattcca attggaattg acaaagctct ggagaaaatg     780
cagcgggaag aacaatgtat tttatatctt ggaccaagat atggttttgg agaggcaggg     840
aagcctaaat ttggcattga acctaatgct gagcttatat atgaagttac acttaagagc     900
ttcgaaaagg ccaaagaatc ctgggagatg gataccaaag aaaaattgga gcaggctgcc     960
attgtcaaag agaagggaac cgtatacttc aagggaggca atacatgca ggcggtgatt    1020
cagtatggga agatagtgtc ctggttagag atggaatatg gtttatcaga aaaggaatcg    1080
aaagcttctg aatcatttct ccttgctgcc tttctgaacc tggccatgtg ctacctgaag    1140
cttagagaat acaccaaagc tgttgaatgc tgtgacaagg cccttggact ggacagtgcc    1200
aatgagaaag gcttgtatag gagggtgaa gcccagctgc tcatgaacga gtttgagtca    1260
gccaagggtg actttgagaa agtgctggaa gtaaaccccc agaataaggc tgcaagactg    1320
cagatctcca tgtgccagaa aaaggccaag gagcacaacg agcgggaccg caggatatac    1380
gccaacatgt tcaagaagtt tgcagagcag gatgccaagg aagaggccaa taaagcaatg    1440
ggcaagaaga cttcagaagg ggtcactaat gaaaaaggaa cagacagtca agcaatggaa    1500
gaagagaaac ctgagggcca cgtatgacgc cacgccaagg agggaagagt cccagtgaac    1560
tcggcccctc ctcaatgggc tttcccccaa ctcaggacag aacagtgttt aatgtaaagt    1620
tgttatagt ctatgtgatt ctggaagcaa atggcaaaac cagtagcttc ccaaaaacag    1680
cccccctgct gctg                                                      1694
```

<210> SEQ ID NO 10
<211> LENGTH: 459
<212> TYPE: PRT
<213> ORGANISM: Homo sapiens

<400> SEQUENCE: 10

```
Met Thr Ala Glu Glu Met Lys Ala Thr Glu Ser Gly Ala Gln Ser Ala
  1               5                  10                  15

Pro Leu Pro Met Glu Gly Val Asp Ile Ser Pro Lys Gln Asp Glu Gly
             20                  25                  30
```

-continued

```
Val Leu Lys Val Ile Lys Arg Glu Gly Thr Gly Thr Glu Met Pro Met
         35                  40                  45

Ile Gly Asp Arg Val Phe Val His Tyr Thr Gly Trp Leu Leu Asp Gly
     50                  55                  60

Thr Lys Phe Asp Ser Ser Leu Asp Arg Lys Asp Lys Phe Ser Phe Asp
 65                  70                  75                  80

Leu Gly Lys Gly Glu Val Ile Lys Ala Trp Asp Ile Ala Ile Ala Thr
                 85                  90                  95

Met Lys Val Gly Glu Val Cys His Ile Thr Cys Lys Pro Glu Tyr Ala
             100                 105                 110

Tyr Gly Ser Ala Gly Ser Pro Pro Lys Ile Pro Pro Asn Ala Thr Leu
         115                 120                 125

Val Phe Glu Val Glu Leu Phe Glu Phe Lys Gly Glu Asp Leu Thr Glu
     130                 135                 140

Glu Glu Asp Gly Gly Ile Ile Arg Arg Ile Gln Thr Arg Gly Glu Gly
145                 150                 155                 160

Tyr Ala Lys Pro Asn Glu Gly Ala Ile Val Glu Val Ala Leu Glu Gly
                 165                 170                 175

Tyr Tyr Lys Asp Lys Leu Phe Asp Gln Arg Glu Leu Arg Phe Glu Ile
             180                 185                 190

Gly Glu Gly Glu Asn Leu Asp Leu Pro Tyr Gly Leu Glu Arg Ala Ile
         195                 200                 205

Gln Arg Met Glu Lys Gly Glu His Ser Ile Val Tyr Leu Lys Pro Ser
     210                 215                 220

Tyr Ala Phe Gly Ser Val Gly Lys Glu Lys Phe Gln Ile Pro Pro Asn
225                 230                 235                 240

Ala Glu Leu Lys Tyr Glu Leu His Leu Lys Ser Phe Glu Lys Ala Lys
                 245                 250                 255

Glu Ser Trp Glu Met Asn Ser Glu Glu Lys Leu Glu Gln Ser Thr Ile
             260                 265                 270

Val Lys Glu Arg Gly Thr Val Tyr Phe Lys Glu Gly Lys Tyr Lys Gln
     275                 280                 285

Ala Leu Leu Gln Tyr Lys Lys Ile Val Ser Trp Leu Glu Tyr Glu Ser
290                 295                 300

Ser Phe Ser Asn Glu Glu Ala Gln Lys Ala Gln Ala Leu Arg Leu Ala
305                 310                 315                 320

Ser His Leu Asn Leu Ala Met Cys His Leu Lys Leu Gln Ala Phe Ser
                 325                 330                 335

Ala Ala Ile Glu Ser Cys Asn Lys Ala Leu Glu Leu Asp Ser Asn Asn
             340                 345                 350

Glu Lys Gly Leu Phe Arg Arg Gly Glu Ala His Leu Ala Val Asn Asp
         355                 360                 365

Phe Glu Leu Ala Arg Ala Asp Phe Gln Lys Val Leu Gln Leu Tyr Pro
     370                 375                 380

Asn Asn Lys Ala Ala Lys Thr Gln Leu Ala Val Cys Gln Gln Arg Ile
385                 390                 395                 400

Arg Arg Gln Leu Ala Arg Glu Lys Lys Leu Tyr Ala Asn Met Phe Glu
                 405                 410                 415

Arg Leu Ala Glu Glu Asn Lys Ala Lys Ala Glu Ala Ser Ser Gly
             420                 425                 430

Asp His Pro Thr Asp Thr Glu Met Lys Glu Gln Lys Ser Asn Thr
         435                 440                 445

Ala Gly Ser Gln Ser Gln Val Glu Thr Glu Ala
```

-continued

<210> SEQ ID NO 11
<211> LENGTH: 2156
<212> TYPE: DNA
<213> ORGANISM: Homo sapiens

<400> SEQUENCE: 11

```
cccggcctcc cgcacgcccc gcaggtagcg cccccgcccg cggcccagag tgcgctcgcg      60
ccggcaccag ctcccggata aacggcgcgc cgcgcggaga tgacagccga ggagatgaag     120
gcgaccgaga gcggggcgca gtcggcgccg ctgcccatgg aggagtggga catcagcccc     180
aaacaggacg aaggcgtgct gaaggtcatc aagagagagg gcacaggtac agagatgccc     240
atgattgggg accgagtctt tgtccactac actggctggc tattagatgg cacaaagttt     300
gactccagtc tggatcgcaa ggacaaattc tcctttgacc tgggaaaagg ggaggtcatc     360
aaggcttggg acattgccat agccaccatg aaggtggggg aggtgtgcca catcacctgc     420
aaaccagaat atgcctacgg ttcagcaggc agtcctccaa agattccccc caatgccacg     480
cttgtatttg aggtggagtt gtttgagttt aaggagaag atctgacgga agaggaagat      540
ggcggaatca ttcgcagaat acagactcgc ggtgaaggct atgctaagcc caatgagggt     600
gctatcgtgg aggttgcact ggaagggtac tacaaggaca agctctttga ccagcgggag     660
ctccgctttg agattggcga gggggagaac ctggatctgc cttatggtct ggagagggcc     720
attcagcgca tggagaaagg agaacattcc atcgtgtacc tcaagcccag ctatgctttt     780
ggcagtgttg ggaaggaaaa gttccaaatc ccaccaaatg ctgagctgaa atatgaatta     840
cacctcaaga gttttgaaaa ggccaaggag tcttgggaga tgaattcaga agagaagctg     900
gaacagagca ccatagtgaa agagcggggc actgtgtact caaggaagg taaatacaag     960
caagctttac tacagtataa gaagatcgtg tcttggctgg aatatgagtc tagttttttcc    1020
aatgaggaag cacagaaagc acaggccctt cgactggcct ctcacctcaa cctggccatg    1080
tgtcatctga actacaggc cttctctgct gccattgaaa gctgtaacaa ggccctagaa    1140
ctggacagca caacgagaa gggcctcttc cgccggggag aggcccacct ggccgtgaat    1200
gactttgaac tggcacgggc tgatttccag aaggtcctgc agctctaccc caacaacaaa    1260
gccgccaaga cccagctggc tgtgtgccag cagcggatcc gaaggcagct tgcccgggag    1320
aagaagctct atgccaatat gtttgagagg ctggctgagg aggagaacaa ggccaaggca    1380
gaggcttcct caggagacca tcccactgac acagagatga aggaggagca gaagagcaac    1440
acggcaggga gccagtctca ggtggagaca gaagcatagc ccctctccac cagccctact    1500
cctgcggctg cctgcccccc agtctcccca ctccaccctg ttagttttgt aaaaactgaa    1560
gaatttgag tgaattagac ctttattttt ctatctggtt ggatggtggc tttaggggaa    1620
gggggaaagg tgtaggctgg gggattgagg tggggaatca ttttagctgg tgtcagcccc    1680
tcttcccttc ctccattgca catgaacata tgtccatcca tatatattca tcagaatgtt    1740
aatttatttt gctccctctg ttaggtccat tttctaaggg tagaagaggc aagtggtagg    1800
gatgaggtct gataagaacc cagggtggag agggagactc ctgggcagcc gttttcctca    1860
tcctttccct ctcccagtcc atttccaaat gtggcctcca tgtgggtgct agggacatgg    1920
gaaaaaccac tgctatgcca tttcttctct ctgttccctt cctcaccccc gacggtgtgg    1980
ctgatgatgt cttctggtgt catggtgacc acccctgtt ccctgttctg gtatttcccc    2040
tgtcagtttc ccctctcggc caggttgtgt cccaaaatcc cctcagcctc ttctctgcac    2100
```

```
gttgctgaag gtccaggctt gcctcaagtt ccatgcttga gcaataaagt ggaaac        2156
```

<210> SEQ ID NO 12
<211> LENGTH: 370
<212> TYPE: PRT
<213> ORGANISM: Homo sapiens

<400> SEQUENCE: 12

```
Met Ser His Pro Ser Pro Gln Ala Lys Pro Ser Asn Pro Ser Asn Pro
  1               5                  10                  15

Arg Val Phe Phe Asp Val Asp Ile Gly Gly Glu Arg Val Gly Arg Ile
                 20                  25                  30

Val Leu Glu Leu Phe Ala Asp Ile Val Pro Lys Thr Ala Glu Asn Phe
             35                  40                  45

Arg Ala Leu Cys Thr Gly Glu Lys Gly Ile Gly His Thr Thr Gly Lys
         50                  55                  60

Pro Leu His Phe Lys Gly Cys Pro Phe His Arg Ile Ile Lys Lys Phe
 65                  70                  75                  80

Met Ile Gln Gly Gly Asp Phe Ser Asn Gln Asn Gly Thr Gly Gly Glu
                 85                  90                  95

Ser Ile Tyr Gly Glu Lys Phe Glu Asp Glu Asn Phe His Tyr Lys His
                100                 105                 110

Asp Arg Glu Gly Leu Leu Ser Met Ala Asn Ala Gly Arg Asn Thr Asn
            115                 120                 125

Gly Ser Gln Phe Phe Ile Thr Thr Val Pro Thr Pro His Leu Asp Gly
130                 135                 140

Lys His Val Val Phe Gly Gln Val Ile Lys Gly Ile Gly Val Ala Arg
145                 150                 155                 160

Ile Leu Glu Asn Val Glu Val Lys Gly Glu Lys Pro Ala Lys Leu Cys
                165                 170                 175

Val Ile Ala Glu Cys Gly Glu Leu Lys Glu Gly Asp Asp Gly Gly Ile
            180                 185                 190

Phe Pro Lys Asp Gly Ser Gly Asp Ser His Pro Asp Phe Pro Glu Asp
        195                 200                 205

Ala Asp Ile Asp Leu Lys Asp Val Asp Lys Ile Leu Leu Ile Thr Glu
    210                 215                 220

Asp Leu Lys Asn Ile Gly Asn Thr Phe Phe Lys Ser Gln Asn Trp Glu
225                 230                 235                 240

Met Ala Ile Lys Lys Tyr Ala Glu Val Leu Arg Tyr Val Asp Ser Ser
                245                 250                 255

Lys Ala Val Ile Glu Thr Ala Asp Arg Ala Lys Leu Gln Pro Ile Ala
            260                 265                 270

Leu Ser Cys Val Leu Asn Ile Gly Ala Cys Lys Leu Lys Met Ser Asn
        275                 280                 285

Trp Gln Gly Ala Ile Asp Ser Cys Leu Glu Ala Leu Glu Leu Asp Pro
    290                 295                 300

Ser Asn Thr Lys Ala Leu Tyr Arg Arg Ala Gln Gly Trp Gln Gly Leu
305                 310                 315                 320

Lys Glu Tyr Asp Gln Ala Leu Ala Asp Leu Lys Lys Ala Gln Gly Ile
                325                 330                 335

Ala Pro Glu Asp Lys Ala Ile Gln Ala Glu Leu Leu Lys Val Lys Gln
            340                 345                 350

Lys Ile Lys Ala Gln Lys Asp Lys Glu Lys Ala Val Tyr Ala Lys Met
        355                 360                 365
```

Phe Ala
370

<210> SEQ ID NO 13
<211> LENGTH: 17133
<212> TYPE: DNA
<213> ORGANISM: Homo sapiens

<400> SEQUENCE: 13

| | | | | | |
|---|---|---|---|---|---|
| attatgaaaa | aatttaaatg | tgcaaaataa | agaagagtag | tataataaac | tcccatgcac | 60 |
| caatcatctg | cctggccctt | atgtttcatc | cacaacccaa | cccacttacc | tgactccagg | 120 |
| ttattttaaa | acaacttcag | gcactatagc | atctaattt | cagtaattta | aaaaagagtg | 180 |
| tataagaatg | ctttagagat | tacaaggcaa | atgcttacac | attatctttt | tccattctca | 240 |
| taccctgttc | tttggcactt | taccgaaaag | gaaatgagaa | gggttcagag | aaattaaatg | 300 |
| acttttcttt | ggtaacatgc | ctagtataca | tgtagtcaga | acttgaagct | tttgcttttt | 360 |
| ttttttcttt | tttaacatca | actttcgtgc | ttagtccagt | gtataacatc | acaggcaaat | 420 |
| tcaaattgag | aataggaatc | agttgttctt | taaccgtaac | ccttctaact | tttacttatc | 480 |
| ctaagaccgg | gtagcaagta | gggcaggagc | cttcatctag | agggatggtg | acagctctga | 540 |
| taggggaaaa | ttagcactgg | tctttccttc | caaaaagcca | ctctggctgc | tgctgttgac | 600 |
| acaaggctcc | tggcttttga | gacattattt | gagtgctgga | ttccaatact | ttttactttc | 660 |
| tcataagaaa | aaaaaatgtg | aagcatctaa | ggatatctcc | tgccttattg | ataaagtaag | 720 |
| cctcaggctg | aatccaaatt | gctgagctcc | aatagaacta | cagggcaaag | catctacaca | 780 |
| gggaattgcc | actcttctcc | aaaattaggc | tttattaaga | gcaaggcta | tgttctcctc | 840 |
| atatatatgt | gtgtgtgtgt | gtgtgtgtgt | gtgtgtgtgt | gtgtgtgtgt | aaaaagtaaa | 900 |
| tgttttacac | agatccccat | aagggaaaag | tgggctatag | taatacagta | ttttttttgtt | 960 |
| tttcttttt | ttgggggggg | gggacagttt | cgctctgtca | cccagtctgg | agtacagtgg | 1020 |
| cgcgatctcg | gttcactgca | accgccgcct | cccgggttca | agcgattctc | ctgcctcagc | 1080 |
| ctcccgagta | gctgggacta | caggcaagca | ccaccacgcc | cgggtgattt | ttttttttt | 1140 |
| tattttagt | agagacgggt | ttcatcatgt | tggtcaggct | ggtctcgaac | tcctgacctc | 1200 |
| aaatgatccg | cccgcctcgg | cctcccaatg | tgctgggact | acaggcgtga | gccaccgcgc | 1260 |
| cccgccaaat | acagttttat | caggaatcaa | aactgtgctc | tcttctggac | tctcagcttt | 1320 |
| agctgtttgg | agcgtttagt | ctaagcctta | ccacttacat | tgtaatgtga | agatcaaatt | 1380 |
| gtaacgacat | ggcaataata | aggctcctat | tggttgggta | ccaccagttt | atgccaggca | 1440 |
| ttgtactgat | tcatgtcttt | aatcctcaaa | acgaccttcc | gaggtcagcg | ttttattct | 1500 |
| ttttccagag | gagcaaactg | agtttctgag | aagtcacacc | caacttggtg | gcagagctga | 1560 |
| cgctggcatg | gggttgactc | caaagctctc | tacgccacga | gggtgggaaa | gacaacgaaa | 1620 |
| cacaagcgag | aagaataatg | agaactggga | tcgcaacttc | attaaatgag | aagccaggaa | 1680 |
| caggtggcgg | agggcacgcg | gttcgctgca | cggagtcgct | caggctcttt | gaaacaccgc | 1740 |
| gcgggggagc | ggggcggtgc | cggaagtcag | gccatggctt | ccggttcttg | cgtcggaagt | 1800 |
| ggccggtcag | cgtcgctgcc | ggtctccggc | ggagacggac | tctggagttt | gggcggcccg | 1860 |
| ggcggccact | aggtactctg | atattccgta | ctaaacacgt | ctgcaagtca | agatgtcgca | 1920 |
| cccgtccccc | caagccaagc | cctccaaccc | cagtaaccct | cgagtcttct | ttgacgtgga | 1980 |
| catcggaggg | gagcgaggtg | agcggagtct | gacgctcgcg | gaaaagcccc | gaggaggcgg | 2040 |

```
gggttcccgg gatttggggg attccaaggg cggaatgcgg ctccggccgg tgactgctca    2100
gtttcgcgga ggggatggct gcctaggctg gtccgccgga gcaggcccgg agatctaggg    2160
ctagatcgat ccagcgccct tgtatcaatg ccatcggtgg tgcggaagtt tctggaaatt    2220
tctagttcgg gaattgtggc gtcctttagg tttgcctcct gatttggtgg cacttccacg    2280
ccacctttgc actaccaagt tagcatgaaa tattttatgt ttgcaatggg acagttcgga    2340
aagcatatcc tgggatatgc gtctgctggg ccccaggaaa ctatatttgc cacatgagat    2400
aatatatcag cacgtgctgt gttatttata cgttaaaggg acttgttttgc tcattgcttt    2460 tgccttatta ctgattctta atttagaggt ccgttcagat gagcaaacat tttctcttaa    2520
tttgccattg ggaaaatgcg ctcaacgtag tgatggtgtt gcctaggtta catagccgct    2580
cagaagttcc taaggcctgg tgaattaggg agcgtgttgc tttgtaactg gattggcctt    2640
gttctggaac acgttggaat tgctggccag gcaatgtgtt tgaatgcatg tacaggacac    2700
acacacgttt acacgtacat tcagtttgtt gcaactagct agggctaggt ttaatctcac    2760
ctgtcttagc tgctatctag aggaggaatt tttacagctt ttgcttcaga ggttgcatga    2820
ggcagtttgc tcagagcaca aaggctgcag gtatacgtaa cacgtggcaa gtccgcccac    2880
ccaaagactg tttaattttc tcccgttggt tgcttggtga ttggaaattc tcagtacctc    2940
ttgaagaaat tactcaggat ttaaaactat ttgtatttaa tgatatctct tacatggtgc    3000
taatcttttg gctactataa ttggttatga tccttagtgt aatgtttcaa atctgtttat    3060
atacatacat gacagtaggt agactaaatt tgaatattag aataaaataa gattcactaa    3120
ttctagtgag tatattcaaa ggaaatgaag tttgtatgtc aaagaggtat ctgcactccc    3180
atgttcattg cagcattatt catgatagcc aagataatgg aatcaaacta ggtttccatc    3240
tacagatgga ttttttttaa aatttgatat atgtgcacag tggagtacta ttcacccata    3300
aaaaataatg aaatcttgtc acttctgaca acatgaatta atatgcagga cattatgtta    3360
catgaaataa gctgggcaca ggaagacaag gcatgatctc acttacatgt ggtttctaaa    3420
aagttgacct tgaagtagag aatggaatgg tggatttcag gggttgggta gatgttgatc    3480
acgagagacc taatttcagt tagaaagggg gaataaattt aagagatcta tgtataaca    3540 taatgactat agttagtagc aatgtgttgt gttcttgaaa ttgcaaaaaa gaaaaattac    3600
agtaaagggg aacttggtaa ttcatgattg atctgctacc ataattatac caaccttctt    3660
tttatcattt gtctatttgg ttgttttgca tactgacaag atttttctttt cttttagttg    3720 gtcgaattgt cttagaattg tttgcagata tcgtacccaa aactgcggaa aattttcgtg    3780
cactgtgtac aggagaaaaa ggcattggac acacgactgg gaaacctctc catttcaaag    3840
gatgcccttt tcatcgaagt atgtgtaaat tttcttaatc ttgttattct tcatacagac    3900
aagtcctgtt ctttaggatt tggggaagaa acactaagt aggaagtgaa gcttaaaaag    3960
tactattagc gtccatgtct gaggcagtaa cgcagtttcg taaaggttag gctgtgcgag    4020
gtggaattac ttatggtact aaggtttatc tatagagaaa tggactcccc tagctttacc    4080
catcctctca ttctccttca ctctaagatg atttgattga gaaaggaagg ccgtagtcaa    4140
ccaaccttag gtagcttcat tgcctggtga caaaaaagtt atgcatagac cgggcgcagt    4200
ggctcacgcc tgtaatccca gcactttggg aggctgaggc gggtgaatca cgaggtcagg    4260
agatcgagac catcttggct aacgcggtga accccgtct ctactaaaaa tacaaaaaat    4320
aagccgggtg tggtggtggg cgcctgtagt cccagctact cggaggctg aggcagtaga    4380
```

-continued

```
atggcatgaa ctcagaaggt ggagcttgca gtgagccgag atcacgccac tgcactccat    4440
cctgggcgac agagtgagac tctgcctcaa acaaacaaac aaacaaacaa acaaaaaaat    4500
gcataatttt tgggcctgag tgcttgggaa ggcagcagat ttgaagattc agtgttttgg    4560
gcacatgggt gatagtgtgg tcaaaatatg ccatttcata ctgcttatta cactttgtaa    4620
tgaatcatac ttttgtttag tgataatggt tctcccaata gactgcaggc tctatgagtt    4680
caagaactgt atgttttcac cattttgttt ttggcatcta atacagttat tgagtaagaa    4740
ctcagtaagt atttgtttaa taaataggca aataagcaat aatcacaaga gcaacatttt    4800
ttaaacgatt tattaagaaa aaattaactt tttaaaaata tttaaaatgt ttactttcat    4860
gtttaataaa aacttgaaat atgctaataa actatatgca gaaatatttt aacatagcaa    4920
gtgtgagact gctatcttta gaaaggtctg cctgcaagag tagcacttgt ttggagtctg    4980
ggaacttgac acttgtacca tttcctaaat agtaatggtg atttactatg cctagcctat    5040
ttgtacaaac atgaatgtgt gctctctttt ggggagtctg gaattttggt acatgctagg    5100
tagagtgtgc ccaataaata ccttgggtgc tgagtctcta attggctctc ctgggcagaa    5160
atactgtgta catgttgctg catttttgtt gctgggggaa gtgtgtgttc tgtagcactt    5220
catgggacgg agaaagcata aggaagcctg cacatggatt tttccagact ctgcctgtgt    5280
ctttcccgtc atctcgctgt gtatccttac cactgtgatc caaccacata ctgatttgtg    5340
tgagctctag ggttctctga acatgaaagc aatcttggta acctttgaca caaagtgata    5400
tatttgctga aaattttcca ttagggtaga acaaatctac tgggaatcat tggtctgtat    5460
tcagcagaca ttattgagta actaatatgt actatgtgta catgcacata gttataagga    5520
tgtaaaacaa tacagttggt gtacttaagg agatcattgc tggaaggggc agatcataat    5580
gccatatgtt atgtaggcag agtcaagata ctatgggaga aaaattagga catacagctt    5640
agggatttca gtgacagttt tataggggag gtatcatttg aaccgatttt ctgaatgtta    5700
gcagggatca ggcagtgaaa ataggttgga ttcagatggt gaaaagcctg aagcgtttgg    5760
agttgcggag acgggtgggg agggacaaac aggagagaga catgactaga gtcatgcact    5820
acaaagttgt cttacgtacg tatccattag taagcattgc taaaggcatc catgtctcag    5880
tcactaatag ccattttcct tttttgtagt tattaagaaa tttatgattc agggtggaga    5940
cttctcaaat cagaatggga caggtggaga agtatttat ggtgaaaaat ttgaagatga    6000
aaatttccat tacaaggtaa agtagagaaa atgcatgtta ttgctgataa aaagattgtt    6060
atatatctgg aatacttgtt ggattaagac accaaaaaat gtttcaagtg tgcttagatt    6120
ctccatttct tgtaatagga atcacttttg taaataatgg ttctttaata tggaaaagtt    6180
ttcattcagt aatgattaat tcagcattat ttcattgtga tccagttttt atatgcttca    6240
gttaagccag tgagttttta aatgcgacca gcatctggca aaattgtttc caggaaaaat    6300
gtttccattg ttgaaggat ggtaacttgt gcatccttat ccttgaatgt gaagagcaac    6360
aaaaccatca ctaatatcca ggatgtcagg ggatttgcac actagcagat atagttaaat    6420
gtccaagctc ctaaaggact tcagtggtgc ctgtgccttc ttgtcttcgt tgtcccaaga    6480
tgtaattggg gtatattgca tcattcaagt tataagaatg gacatgtaag tacaaaagta    6540
aagtgatatt tttggaaata aggaaatgaa gcaaggtat taggataatt tgaaaaaatg    6600
tcgtcagtct tccagtcagt gtttattgag ccactatcac tggcaccaaa gggtttataa    6660
aaatgaaagg ccttgatgac aaggaattta taatcctacc tcagagacaa gattaagata    6720
catgggacta ctggagaata atagtatata aataaatgct aaattgattg aatatccttg    6780
```

-continued

```
cttgtataac attgctaata ctgtctatat actgcaggag aaagatgtga tttatgcagt    6840
ctgaattatt atggaagtca ttgaggagga atggctactt gggctgtgca gactgggtct    6900
tgcaaggcgg caacatgtct gagatttggt taggcaggaa ctgtagtatt gatgcagaat    6960
ttaaaagggg acgtcggtga ggaaagacaa aggcaagaga cgttgaggaa ataaagttct    7020
agttactgtt gtaccaaagg aagctaccag aaggatgaaa actaaaggtg atgtgatgat    7080
cacattgaca tagagaaaag gggcctatag acaagacaca tgattcttgc tttctataaa    7140
cgtggtggcc ttaaaatctg aatttgattt agactgaggg gagtaaaagg cattttggtg    7200
gggtgggggg tgtcatgaaa cattatataa catgagagtt acggtgcatg caccaacaag    7260
gaatacattt agaaagccta ggagataaag tgaaaaggtt aagaaattgg gtttcataga    7320
tcctttgaca ggattatgcc aaggtagaat tttgatttca agatgtatgc agcagtttct    7380
tttgagcact ctccgaagag gtgattcatc tgggatgaaa acctaatcca aatcctgtat    7440
gatttggatt cttttgagat taggaaagta ccaaactgaa tgtcttgggt aaattcagta    7500
tcccattatt gttccagttt attgatgttt tgtaaaggaa gacttatact gtaggcatat    7560
ttatgaattt ggaagaccgt tcaggtcttc ccagaaaaaa agagcattca tcataaagag    7620
ggcaaaatat attacaagag tttcataatg ctgcatcttc attttaaagg tgaagtgtaa    7680
gtattttctc atggccaatt tagaaataac cctcccccg actattgttt ctgttaccta     7740
tttactttga taaggttttt taaagtttaa agtgattaag tgcccatgt tttgtgaatt     7800 aaaggttgca gtttataaaa aaataaaaag taattaaaaa atttttataag tgaaaagtaa    7860 aaaaaagtag tttgatctaa atggtagtat agtgcacccc agttttatgt tcagtaaaag    7920
aacagttcag actaacacac aattcagaaa agaacacatc taaccttggt tttcttttaa    7980
tttttatttc tacagcatga tcgggagggt ttactgagca tggcaaatgc aggccgcaac    8040
acaaacggtt ctcagttttt tatcacaaca gttccaactc ctcatttgga tgggaaacat    8100
gtggtgtttg gccaagtaat taaggaata ggagtggcaa ggatattgga aaatgtggaa     8160 gtgaaggtg aaaaacctgc taaagtaagt aaaaagttac agtgaaatac acttattatc     8220
ttagttgcta tcttttgag acggagtctc gatctgttcc aggctggagt gcagtggtgc     8280
ggtctcggct cactgcagcc tctgtctccc aggttcaagc tattctcctg cctcagcctt    8340
ctgagtagca gggattacag gcgcgcgcta caacacccgg ctaatttttt ctgtattttt    8400
aatagagacg gggtttcacc atgttggcca ggctggtctc aaactcctga ccttgtgatc    8460
cgcccacctc ggcctcccaa agtgctggga ttacaggcat gagccaccgc acccagcctg    8520
ttagttgcta tcttaaagaa atataagtaa aaggatcagg tgattattag ctggaaaaat    8580
gttataataa ttttgggtat aggagccagg atctgccact tttttttttt ttttttaact    8640
tttctacaat gggaaagaca attagggtag ttttaaagga gatttttatt atttcaactt    8700
tcatttggtg atctttgcta gtttacgtta agtcttccta tacctgcaaa actgttcagt    8760
tggtatgtat agtagtacat agtggaatga ggataataag cccaaaatct tgtctggatt    8820
gtagcattaa ctagaggctt ggccttgact ttgttactta acttttccac acgtgttttc    8880
tcctgtctaa attacttatg ggtttagact agattatctc tgaagaccct tgtgtactta    8940
atgtctgtga atcaaaatga ccttaatatt ggctgggcat ggtagctcat gcttgtaatc    9000
ccagcacttt gggaggctga ggtgggagga tcacttgaga ccaggagttg gaaaccagct    9060
ttggcaacat agtgagatgc tgtctctatt aaaaaaaaaa gaaaaaagaa aaaccctaa     9120
```

-continued

```
acgaccataa tactacccag cctaagtgac agggttgtga gtgggagttg gaagctcagt   9180
tacttgtagg aggtaggctg tcactcagtg tatgacaaga atagtagtaa accggaagct   9240
catgccccac ctaatgccac ttacatagac aatgataaaa ttgccaactt attctgtgtt   9300
tattgagctc ctgaatagca ataaaatgct tatgtaaata ctaacattgt cgtattagtt   9360
ggaatgtata aaaacagcat tatagtacat aaatgagcct tctcacataa atctgtgaat   9420
tggacagtgc tgcacatgac ttcagctgta tagcttttat ctctcattat tacgatagtg   9480
cacttctaca atttagggtt attttttacag ttgtgcgtta ttgcagaatg tggagaattg   9540
aaggaaggag atgacggggg aatattccca aaagatggct ctggcgacag tcatccagat   9600
ttccctgagg atgcggatat agatttaaaa gatgtgagta ctttcagatt agtcaaactt   9660
taattaattt agtaagtgaa aatatttagt actaaaagtt tgagcttttg tttcagtctc   9720
tcatatgata gaatctagca ttaaaccaca ttacttacta aaatccaaca tatttgtatt   9780
tttttataca ggtagataaa attttattaa taacagaaga cttaaaaaac attggaaata   9840 ctttttttcaa atcccagaac tgggagatgg ctattaaaaa atatgcagaa gttttaaggt   9900
aatattattt ctaacaaatt attttttaaga aattataaat tgaattataa actaaaatta   9960
agaattgctc attatatttt tgcaaattac ttgtggaata accaggtgtg ttgaaatagt  10020
tgcatttcct ttttttttccc tcagcttgtt ttgagaaatt tcaaaagaca gaagttgaac  10080
gagtagtaca taattactca taagttttac ttacattcac caatttttaa cttttgctgt  10140
ttacgttttt acagaactat tttgataggga agttgttgat actgtgatac tttaccctaa  10200
gtatttcagc acgtatttcc taagaaacaa agacattctg cataagttca ataccgttaa  10260 aacacccccaa agtaatattg atagataata tcaatccata tttaggctgg gcatagtggc  10320
tcatgcctat aatcccagca ctttgggagg ccaagctggg cggatcacct gaggtcggga  10380
gttcgagacc agcctggcca atatggtgaa acccccatctc tactaaaaat acaaaaatta  10440
gctgggctgg tggcgcacgc ctgtaatccc agctacttgg gaggctgagg cacaagaatt  10500
acttgaaccc aggaggtgga ggttgcagca agccgagatt atgccactgc actccagcct  10560
gggcgacaga gtgagattct gtctcaaaaa aaaaaaaaaa agtaatccat attccaactt  10620
ccccagttgt ttcaatttct tagaaaaatc aagggtccaa actaagatta tgtgttatat  10680
ttagtggtag tatctcttac gtttcctacc tccctggtt ttttattcat ttgcatttt   10740 gtggagtcca agtcagttgt ttttatagac ttccatctgt atgtgtttgt ttccttaaga  10800
ttagtttgag gtgaaatatt ttggcaagaa gacttaggtg ttgttttgta ttacctatga  10860
tatcacatcc tgaagacaca tttcgctttg gcctgtttga gttcacacac atggttaaag  10920
tagtgtcagc cacaagcatt tgttagtctg aggtggtatc gtgaaattgt atgaatttct  10980
agtccccaac aacttttcac acagtggatc ttagcatcat tgaaaatcca tgcctgaatc  11040
tgttatactg aacttctaag tttatcatcg tacagttatt aactagcatt cttctgtttg  11100
cgagagcctc ccgcatattt tttaagtatc actatagacc tgtggatatt tttctttttct  11160 tttttttttcc ttttatagaa acaaggcctc ctttatattg cccaggctgg tctgaaactt  11220
ttgggcccaa gcaatcctcc ctcctcacct tcccaagtag cagggactag aggatatctt  11280
atgggtagtt ttcaattccg tttgttagta cgctattatt gtcattcttt ttcatgccca  11340
aagggttcca aatttgttca gtggaaggcc ccttttccttt ggcatgttcc tattagtctg  11400
cgagcacttg cttgctctaa gctcatcttg ccttactttc agatctgata tggcagtttc  11460
tccaaggacc tctgatttct tttagagaaa gaaaacttta gaaaccaaat tctgggggcc  11520
```

-continued

```
aggtgtgctc agttttgggg ccctttcag ggacaatgca aaatcaacac aatagagttc      11580
tccttcatct ttcctctact gaattccctt ctcctattat gagaatcctg gttccaaaca      11640
taattatgtt ggaaagtaca tagtggggac ctgagtttta aaaatagaaa agtgttacta      11700
gtgcataatt agatttggga attgctctta aattggcctc tttgaacact ttggggaaca      11760
aaaacaattt tttttaagcc ttcttaaaaa tttaaaaag tgtgatcatt aagattatta      11820
atagcatttt tagagctttt tatatcagaa atgacataac acttctggac atagagaaga      11880
gtaattcctg tttatgtggt ctttcatact gctttatta atgcattctg cagatacgtg      11940
gacagttcaa aggctgttat tgagacagca gatagagcca agctgcaacc tatagcttta      12000
agctgtgtac tgaatattgg tgcttgtaaa ctgaagatgt caaattggca gggagcaatt      12060
gacagttgtt tagaggtaag tctgtttgat tttgaacttt ttgaataagt tggattaaga      12120
cttagtttga atagtagcaa cttttatata cattaatata tcttattgca taggacctaa      12180
tgaggcttaa gaaaacattt tgtttctaaa tattttggac cctcagttct ttctctacat      12240 tcatttgct tataactctg tgtcacttaa cagctatgaa gatccttgcc ttttttctc       12300 aaagcacata tatcagctca tgtattcact taagagcacc tattgtgtgt taggcattag      12360
aagacaaagt cagaaatgat taagatgtgg gttatggagt cagtcaggca tggcttttt      12420 cttcttcttt tttttttgag acggagtctt actctgttgc ccaggctgga gtgcagtggc      12480
gcaatctcgg cttactgcaa cctctgcctc ccgggttcaa gtgattctcc tgcctcatcc      12540
tcccaagtag ctgggattac aggcatgtgc caccatgccc agataatttt tgtattttta      12600
gtagagacag gtttcacca tgttggccag gctggtctca aactcctgat ctcaggtgat      12660
ccacccgcct tggcctccca aagtgctagg attacaggtg tgagccaccg tgaagtagtt      12720
atagagagtt atataacaca atgtaaggca tttagtgtag tgcctggcac atttaagca      12780 cctaacagag acgagttatt ttaattaaaa gatccatacc ctcaagaagc ttaataagtg      12840
attcaggata ggagggggtc agtttcaatt taggttcatc aggacttgtg tatggagaat      12900
gggttctatt ggaacaggtc atttatcttt aggaggtcat ccaggtatgc taactgataa      12960
agctagaaag gtggcagttt taccttcctc aaatagagca attatgactc tcttccctgt      13020
tgtatagttt gaaaagtttt ccaaatgaaa ctttaagaat tttacatatt aagccaggca      13080
cctagactag ctatgctcag agcaagtaga actaaaatga gatcctaatt ttgtagggta      13140
gatggaataa gggataggaa tatatttaga agggatcata caacagagga aaaaacttat      13200
caaaagaaaa gatgggtctt cactctgggt ttttttttgt tctctgtcac ccatgctgga      13260
gtgcagtgat gcaatcaaag ctcactgcag cctcaacctc ctgggctcgg gtgatcctcc      13320
tacctcagcc tcctaagtag ctgggactac agacccttgc caccatacc agctgatttt      13380 taaatttttt gtagagatgg gttttttgacg tgttgcccag gctggtctct taactcctgg      13440
gctcaagctg tccacccgcc ttggcctcac aaagtgctgg tattatagtt aagagcctct      13500
ctgcccagcc tcgatctctt tttgaccgt gaggcaggta aaatctgagt attggccatt      13560
aaaagatgtt acataaacaa aagataattt taaaatgttt gttctagggg agagacctga      13620
tgcataaagt ctcttaggtt aaaagacctg ttgtaggtaa gaacctaggt tgggtatggt      13680
ggttcatgcc tgtaattcca gcacttaggg aggccacggc ggcgggcaga tcgcttaatt      13740
ccaggagttt gaaaccagcc tgggcaacat ggtgaaaccc tgtctctaaa aaaaaaaaa      13800 aattagtctg gtgtggtggc acatacctgt agtcccagct acttggaggc tgaggtggga      13860
```

```
                                               -continued
ggagcacttg agcctggggg gttgaggcag cagtgagctg tgatcaggcc actgcactcc    13920
agcctgggcc acagagtgag accttgtctt aaaaaaacaa aaaacaaaaa cttaagagtt    13980
tataacttaa gagttattaa gttattaatg ttcctaaaaa acttataatt caagtaaaaa    14040
gtgtatacaa atgtttcttc aaaatgattt tatcttaaaa gtgttagttc aggcccattc    14100
gggagattga aaccacagtg gggagcatat tggaaactag agaaatgtct ttctcctcca    14160
tgtccattca gtgccctctg ctgacaaaac ttagtgccca ctggcagagg agagctattt    14220
gcatgtttca gctccatttt cacagagcag tgaaggatgg gtttggagtt gataggcaat    14280
gaattgaaat ctggcatata agcttaatac tttgatataa atactagctt tatacttttt    14340
tgtaggctct tgaactagac ccatcaaata ccaaagcatt gtaccgcaga gctcaaggat    14400
ggcaaggatt aaaagaatat gatcaagcat tggtaaattt tgttccaaat gtttaatttt    14460
ttaaaataga caactacctt tataaatcat acacctaact taaatgtttt tttccaatta    14520
aaggctgatc ttaagaaagc tcaggggata gcaccagaag ataaaggtaa gttggcagct    14580
tttgtagtga agttaatttt tgttatttaa atacttatcc tcaggaacca ttgttcactt    14640
tgccagattt tagatgtttg ttcaacagac actacagaat gcctgctgtt gggccaggca    14700
ttatcatata gaatgaacaa gacagtcaaa gtccctgccc tcaaagagct tacattctac    14760
tcccattcaa gaatatagta gttttttcacg ttatttattc ttcaagttat catctctgta    14820 gtttttttata tgtctaaata ctgtttgtct tatggtatcc tttgagactg tgttcctatt    14880
ctggttagtc tagtcgagag ctcagcattg taagacacag tattcatggt aaatttaaca    14940
tttgggacca ttcaagttga atgtggctat aaccttagta ttgatgtact ggttatatgt    15000
tttaggaaac tatgacaaaa ataagcttgt ttttcaaata aaccaactat gaatagtgac    15060
actagatctg ggtattacaa aatgtcttttg gtctcttatt actaaaatga aacaagggaa    15120
gcaattactg ttctctaatg tagaggcaga aggcaaatct tgatgtactt gagttctctc    15180
agttgacatc ctctaaaatt acgtttcatt tctgtgtttg tgtgattgct cagattttct    15240
gttactaggg cttagttact ttgtagagaa gttttttcaa ggggtagtta acattaaaat    15300
agtttgttag tcaccataat ttttggatat tttgagaaat aactcacatt gcatatttat    15360
tttacagcta tccaggcaga attgctgaaa gtcaaacaaa agataaaggc acagaaagat    15420
aaagagaagg cagtatatgc aaaaatgttt gcttagaaag gattcagttt tgcttattgt    15480
gtgttgattg tataaatgca ataagaaaat gtaaaggttt ttgtctatga atatgatccc    15540
taatgtgttt cttttgacac cttagttcct tactgtttac agtttaggag tactgatagg    15600
ggttcatgct taataaacat gtcacaatac agtaagtaaa gtggttttgt ttgtttcttt    15660
gagatggagt cttgctctgt cacccaggct ggagtgcggt ggcgcaatct cggctcactg    15720
catcctctgc ctcccgggtt caagcaattc tcctgcctca gcttcccaag tagctgggat    15780
tacaggcacg tgccaccacg cccagctaat ttttgtattt ttagtagaga tggggtttca    15840
ccatattggt cacgtcacgt tggtcttgaa ctcctgacct tgtgatccac cccgccttgg    15900
cctcccaaag tgctgggatt acaggtgtga gccaccgtgc ccggccaagt aaaatgtttt    15960
ttaaaatggt tatgtgcatt attcataaaa aataatggtg tccagtcttt ttaaacttgt    16020
aaagacacat cttattgaat aaagagatga gagcttaagt ttgtatattg tttccttcga    16080
ttctttgatg tatccatggt ggatgatgct aggttttcat acttatagat aatacacaca    16140
cacacacaca cacaatcttg ttcagggatg ggcatacttc ttctgcaagg gccagatcat    16200
aaagttttta ggctttgtag accatgtaat gtcacaccca ctcacctgca cagttgtaat    16260
```

-continued

```
tcaaaattag ccatagacaa tgtgtaacca atgggtattg ctgtgtttca ataaaacttt    16320
agtctagaat atatattcat ttttatattt gattacttaa ctttggcaag tcaaatgtaa    16380
agtccagtag tgaattttgc tcttggtact gaatctctga agaactgaag aggtaggaag    16440
atgctgcatt cttataaagg ttatttaaaa gcaatacccg taatttcttt atgggacaat    16500
cttacatata gtataaaatt tttatttgat aatcattttg tgactattct gttcagtaat    16560
atgcagaaag acattctgaa atctgttaat ctctaaacat tttaacgtta gcttgccata    16620
cttgaaagaa actggctagc tgcagtttac attccattgt aagcaggtcc tcctccacct    16680
tcaggtacca cccagttaat attctgactt ggatctttaa tatcacatgt tttacaatgt    16740
acacagttct gagcatttat ctgtaaccga aatccatcac cttgttccac aggtacaaat    16800
tcataaactc ctgaaaagta aaataaaata atattgaagt gcctaacttt aaaaaatttt    16860
taaattcaaa agtaaaaatt aaggaaagag tagccacaga aaccttaaag gttgctttct    16920
gaatgcttac ccatagagat tatgaagacc ttggtgcatt gctattgatg tgagtgtaaa    16980
ttacatgtac ataataaaag gaggtacagc ggtattcaac tgagttgtct cactatcaag    17040
ggtactcgac actgagtgtt tgagttccac acaacctcga agtcctccct tattcacagt    17100
catcctctca ttcacagggg acaagttcca aga                                 17133
```

<210> SEQ ID NO 14
<211> LENGTH: 1189
<212> TYPE: PRT
<213> ORGANISM: Homo sapiens

<400> SEQUENCE: 14

```
Met Glu Ser Thr Pro Ser Phe Leu Lys Gly Thr Pro Thr Trp Glu Lys
 1               5                  10                  15

Thr Ala Pro Glu Asn Gly Ile Val Arg Gln Glu Pro Gly Ser Pro Pro
            20                  25                  30

Arg Asp Gly Leu His His Gly Pro Leu Cys Leu Gly Glu Pro Ala Pro
        35                  40                  45

Phe Trp Arg Gly Val Leu Ser Thr Pro Asp Ser Trp Leu Pro Pro Gly
    50                  55                  60

Phe Pro Gln Gly Pro Lys Asp Met Leu Pro Leu Val Glu Gly Glu Gly
65                  70                  75                  80

Pro Gln Asn Gly Glu Arg Lys Val Asn Trp Leu Gly Ser Lys Glu Gly
                85                  90                  95

Leu Arg Trp Lys Glu Ala Met Leu Thr His Pro Leu Ala Phe Cys Gly
            100                 105                 110

Pro Ala Cys Pro Pro Arg Cys Gly Pro Leu Met Pro Glu His Ser Gly
        115                 120                 125

Gly His Leu Lys Ser Asp Pro Val Ala Phe Arg Pro Trp His Cys Pro
    130                 135                 140

Phe Leu Leu Glu Thr Lys Ile Leu Glu Arg Ala Pro Phe Trp Val Pro
145                 150                 155                 160

Thr Cys Leu Pro Pro Tyr Leu Val Ser Gly Leu Pro Pro Glu His Pro
                165                 170                 175

Cys Asp Trp Pro Leu Thr Pro His Pro Trp Val Tyr Ser Gly Gly Gln
            180                 185                 190

Pro Lys Val Pro Ser Ala Phe Ser Leu Gly Ser Lys Gly Phe Tyr Tyr
        195                 200                 205

Lys Asp Pro Ser Ile Pro Arg Leu Ala Lys Glu Pro Leu Ala Ala Ala
```

-continued

```
             210                 215                 220
Glu Pro Gly Leu Phe Gly Leu Asn Ser Gly Gly His Leu Gln Arg Ala
225                 230                 235                 240

Gly Glu Ala Glu Arg Pro Ser Leu His Gln Arg Asp Gly Glu Met Gly
                245                 250                 255

Ala Gly Arg Gln Gln Asn Pro Cys Pro Leu Phe Leu Gly Gln Pro Asp
                260                 265                 270

Thr Val Pro Trp Thr Ser Trp Pro Ala Cys Pro Pro Gly Leu Val His
            275                 280                 285

Thr Leu Gly Asn Val Trp Ala Gly Pro Gly Asp Gly Asn Leu Gly Tyr
        290                 295                 300

Gln Leu Gly Pro Pro Ala Thr Pro Arg Cys Pro Ser Pro Glu Pro Pro
305                 310                 315                 320

Val Thr Gln Arg Gly Cys Cys Ser Ser Tyr Pro Pro Thr Lys Gly Gly
                325                 330                 335

Gly Leu Gly Pro Cys Gly Lys Cys Gln Glu Gly Leu Glu Gly Gly Ala
                340                 345                 350

Ser Gly Ala Ser Glu Pro Ser Glu Glu Val Asn Lys Ala Ser Gly Pro
            355                 360                 365

Arg Ala Cys Pro Pro Ser His His Thr Lys Leu Lys Lys Thr Trp Leu
370                 375                 380

Thr Arg His Ser Glu Gln Phe Glu Cys Pro Arg Gly Cys Pro Glu Val
385                 390                 395                 400

Glu Glu Arg Pro Val Ala Arg Leu Arg Ala Leu Lys Arg Ala Gly Ser
                405                 410                 415

Pro Glu Val Gln Gly Ala Met Gly Ser Pro Ala Pro Lys Arg Pro Pro
                420                 425                 430

Asp Pro Phe Pro Gly Thr Ala Glu Gln Gly Ala Gly Gly Trp Gln Glu
            435                 440                 445

Val Arg Asp Thr Ser Ile Gly Asn Lys Asp Val Asp Ser Gly Gln His
        450                 455                 460

Asp Glu Gln Lys Gly Pro Gln Asp Gly Gln Ala Ser Leu Gln Asp Pro
465                 470                 475                 480

Gly Leu Gln Asp Ile Pro Cys Leu Ala Leu Pro Ala Lys Leu Ala Gln
                485                 490                 495

Cys Gln Ser Cys Ala Gln Ala Ala Gly Glu Gly Gly His Ala Cys
                500                 505                 510

His Ser Gln Gln Val Arg Arg Ser Pro Leu Gly Gly Glu Leu Gln Gln
            515                 520                 525

Glu Glu Asp Thr Ala Thr Asn Ser Ser Ser Glu Glu Gly Pro Gly Ser
        530                 535                 540

Gly Pro Asp Ser Arg Leu Ser Thr Gly Leu Ala Lys His Leu Leu Ser
545                 550                 555                 560

Gly Leu Gly Asp Arg Leu Cys Arg Leu Leu Arg Arg Glu Arg Glu Ala
                565                 570                 575

Leu Ala Trp Ala Gln Arg Glu Gly Gln Gly Pro Ala Val Thr Glu Asp
                580                 585                 590

Ser Pro Gly Ile Pro Arg Cys Cys Ser Arg Cys His His Gly Leu Phe
            595                 600                 605

Asn Thr His Trp Arg Cys Pro Arg Cys Ser His Arg Leu Cys Val Ala
        610                 615                 620

Cys Gly Arg Val Ala Gly Thr Gly Arg Ala Arg Glu Lys Ala Gly Phe
625                 630                 635                 640
```

```
Gln Glu Gln Ser Ala Glu Glu Cys Thr Gln Glu Ala Gly His Ala Ala
                645                 650                 655

Cys Ser Leu Met Leu Thr Gln Phe Val Ser Gln Ala Leu Ala Glu
            660                 665                 670

Leu Ser Thr Ala Met His Gln Val Trp Val Lys Phe Asp Ile Arg Gly
        675                 680                 685

His Cys Pro Cys Gln Ala Asp Ala Arg Val Trp Ala Pro Gly Asp Ala
    690                 695                 700

Gly Gln Gln Lys Glu Ser Thr Gln Lys Thr Pro Thr Pro Gln Pro
705                 710                 715                 720

Ser Cys Asn Gly Asp Thr His Arg Thr Lys Ser Ile Lys Glu Glu Thr
                725                 730                 735

Pro Asp Ser Ala Glu Thr Pro Ala Glu Asp Arg Ala Gly Arg Gly Pro
            740                 745                 750

Leu Pro Cys Pro Ser Leu Cys Glu Leu Leu Ala Ser Thr Ala Val Lys
        755                 760                 765

Leu Cys Leu Gly His Glu Arg Ile His Met Ala Phe Ala Pro Val Thr
    770                 775                 780

Pro Ala Leu Pro Ser Asp Arg Ile Thr Asn Ile Leu Asp Ser Ile
785                 790                 795                 800

Ile Ala Gln Val Val Glu Arg Lys Ile Gln Glu Lys Ala Leu Gly Pro
                805                 810                 815

Gly Leu Arg Ala Gly Pro Gly Leu Arg Lys Gly Leu Gly Leu Pro Leu
            820                 825                 830

Ser Pro Val Arg Pro Arg Leu Pro Pro Gly Ala Leu Leu Trp Leu
    835                 840                 845

Gln Glu Pro Gln Pro Cys Pro Arg Arg Gly Phe His Leu Phe Gln Glu
    850                 855                 860

His Trp Arg Gln Gly Gln Pro Val Leu Val Ser Gly Ile Gln Arg Thr
865                 870                 875                 880

Leu Gln Gly Asn Leu Trp Gly Thr Glu Ala Leu Gly Ala Leu Gly Gly
                885                 890                 895

Gln Val Gln Ala Leu Ser Pro Leu Gly Pro Pro Gln Pro Ser Ser Leu
            900                 905                 910

Gly Ser Thr Thr Phe Trp Glu Gly Phe Ser Trp Pro Glu Leu Arg Pro
        915                 920                 925

Lys Ser Asp Glu Gly Ser Val Leu Leu His Arg Ala Leu Gly Asp
    930                 935                 940

Glu Asp Thr Ser Arg Val Glu Asn Leu Ala Ala Ser Leu Pro Leu Pro
945                 950                 955                 960

Glu Tyr Cys Ala Leu His Gly Lys Leu Asn Leu Ala Ser Tyr Leu Pro
                965                 970                 975

Pro Gly Leu Ala Leu Arg Pro Leu Glu Pro Gln Leu Trp Ala Ala Tyr
            980                 985                 990

Gly Val Ser Pro His Arg Gly His Leu Gly Thr Lys Asn Leu Cys Val
        995                 1000                1005

Glu Val Ala Asp Leu Val Ser Ile Leu Val His Ala Asp Thr Pro Leu
    1010                1015                1020

Pro Ala Trp His Arg Ala Gln Lys Asp Phe Leu Ser Gly Leu Asp Gly
1025                1030                1035                1040

Glu Gly Leu Trp Ser Pro Gly Ser Gln Val Ser Thr Val Trp His Val
                1045                1050                1055
```

-continued

```
Phe Arg Ala Gln Asp Ala Gln Arg Ile Arg Arg Phe Leu Gln Met Val
        1060                1065                1070
Cys Pro Ala Gly Ala Gly Ala Leu Glu Pro Gly Ala Pro Gly Ser Cys
        1075                1080                1085
Tyr Leu Asp Ala Gly Leu Arg Arg Leu Arg Glu Glu Trp Gly Val
        1090                1095                1100
Ser Cys Trp Thr Leu Leu Gln Ala Pro Gly Glu Ala Val Leu Val Pro
1105                1110                1115                1120
Ala Gly Ala Pro His Gln Val Gln Gly Leu Val Ser Thr Val Ser Val
                1125                1130                1135
Thr Gln His Phe Leu Ser Pro Glu Thr Ser Ala Leu Ser Ala Gln Leu
        1140                1145                1150
Cys His Gln Gly Pro Ser Leu Pro Pro Asp Cys His Leu Leu Tyr Ala
        1155                1160                1165
Gln Met Asp Trp Ala Val Phe Gln Ala Val Lys Val Ala Val Gly Thr
        1170                1175                1180
Leu Gln Glu Ala Lys
1185
```

<210> SEQ ID NO 15
<211> LENGTH: 3719
<212> TYPE: DNA
<213> ORGANISM: Homo sapiens

<400> SEQUENCE: 15

```
ggaccccct ctgggagagc ccatgaggg caggagagtg atggagagta cgcccagctt      60
cctgaagggc accccaacct gggagaagac ggccccagag aacggcatcg tgagacagga    120
gcccggcagc ccgcctcgag atggactgca ccatgggccg ctgtgcctgg agagcctgc     180
tcccttttgg aggggcgtcc tgagcacccc agactcctgg cttccccctg cttccccca     240
gggccccaag gacatgctcc cacttgtgga gggcagggc cccagaatg gggagaggaa      300
ggtcaactgg ctgggcagca agagggact gcgctggaag gaggccatgc ttacccatcc    360
gctggcattc tgcgggccag cgtgcccacc tcgctgtggc ccctgatgc ctgagcatag    420
tggtggccat ctcaagagtg accctgtggc cttccggccc tggcactgcc ctttccttct   480
ggagaccaag atcctggagc gagctcccctt ctgggtgccc acctgcttgc caccctacct   540
agtgtctggc ctgccccag agcatccatg tgactggccc ctgaccccgc accctgggt    600
atactccggg ggccagccca agtgccctc tgccttcagc ttaggcagca agggcttta    660
ctacaaggat ccgagcattc ccaggttggc aaaggagccc ttggcagctg cggaacctgg   720
gttgtttggc ttaaactctg gtgggcacct gcagagagcc ggggaggccg aacgccttc   780
actgcaccag agggatggag agatgggagc tggccggcag cagaatcctt gcccgctctt    840
cctggggcag ccagacactg tgccctggac ctcctggccc gcttgtcccc caggccttgt    900
tcatactctt ggcaacgtct gggctgggcc aggcgatggg aaccttgggt accagctggg   960
gccaccagca acaccaaggt gcccctctcc tgagccgcct gtcacccagc ggggctgctg   1020
ttcatcctac ccacccacta aggtggggg tcttggccct tgtgggaagt gccaggaggg   1080
cctggagggg ggtgccagtg gagccagcga acccagcgag gaagtgaaca aggcctctgg   1140
ccccagggcc tgtcccccca gccaccacac caagctgaag aagacatggc tcacacggca   1200
ctcggagcag tttgaatgtc cacgcggctg ccctgaggtc gaggagaggc cggttgctcg   1260
gctccgggcc ctcaaaaggg caggcagccc cgaggtccag ggagcaatgg gcagtccagc   1320
```

-continued

```
ccccaagcgg ccaccggacc cttttccagg cactgcagaa caggggggctg ggggttggca   1380 ggaggtgcgg gacacatcga tagggaacaa ggatgtggac tcgggacagc atgatgagca   1440
gaaaggaccc caagatggcc aggccagtct ccaggacccg ggacttcagg acataccatg   1500
cctggctctc cctgcaaaac tggctcaatg ccaaagttgt gcccaggcag ctggagaggg   1560
aggagggcac gcctgccact ctcagcaagt gcggagatcg cctctgggag gggagctgca   1620
gcaggaggaa gacacagcca ccaactccag ctctgaggaa ggcccagggt ccggccctga   1680
cagccggctc agcacaggcc tcgccaagca cctgctcagt ggtttggggg accgactgtg   1740
ccgcctgctg cggagggagc gggaggccct ggcttgggcc cagcgggaag gccaagggcc   1800
agccgtgaca gaggacagcc caggcattcc acgctgctgc agccgttgcc accatggact   1860
cttcaacacc cactggcgat gtccccgctg cagccaccgg ctgtgtgtgg cctgtggtcg   1920
tgtggcaggc actgggcggg ccagggagaa agcaggcttt caggagcagt ccgcggagga   1980
gtgcacgcag gaggccgggc acgctgcctg ttccctgatg ctgacccagt ttgtctccag   2040
ccaggctttg gcagagctga gcactgcaat gcaccaggtc tgggtcaagt ttgatatccg   2100
ggggcactgc ccctgccaag ctgatgcccg ggtatgggcc ccggggatg caggccagca   2160 gaaggaatca acacagaaaa cgcccccaac tccacaacct tcctgcaatg gcgacaccca   2220
caggaccaag agcatcaaag aggagacccc cgattccgct gagacccag cagaggaccg   2280 tgctggccga gggcccctgc cttgtccttc tctctgcgaa ctgctggctt ctaccgcggt   2340
caaactctgc ttgggccatg agcgaataca catggccttc gccccgtca ctccggccct   2400 gcccagtgat gaccgcatca ccaacatcct ggacagcatt atcgcacagg tggtggaacg   2460
gaagatccag gagaaagccc tggggccggg gcttcgagct ggcccgggtc tgcgcaaggg   2520
cctgggcctg ccctctctc cagtgcggcc ccggctgcct ccccaggggg cttgctgtg   2580 gctgcaggag ccccagcctt gccctcgcg tggcttccac ctcttccagg agcactggag   2640
gcagggccag cctgtgttgg tgtcagggat ccaaaggaca ttgcagggca acctgtgggg   2700
gacagaagct cttggggcac ttggaggcca ggtgcaggcg ctgagccccc tcggacctcc   2760
ccagcccagc agcctgggca gcacaacatt ctgggagggc ttctcctggc ctgagcttcg   2820
cccaaagtca gacgagggct ctgtcctcct gctgcaccga gctttggggg atgaggacac   2880
cagcagggtg gagaacctag ctgccagtct gccacttccg gagtactgcg ccctccatgg   2940
aaaactcaac ctggcttcct acctcccacc gggccttgcc ctgcgtccac tggagcccca   3000
gctctgggca gcctatggtg tgagcccgca ccggggacac ctgggaccca agaacctctg   3060
tgtggaggtg gccgacctgg tcagcatcct ggtgcatgcc gacacaccac tgcctgcctg   3120
gcaccgggca cagaaagact tcctttcagg cctggacggg gaggggctct ggtctccggg   3180
cagccaggtc agcactgtgt ggcacgtgtt ccgggcacag gacgcccagc gcatccgccg   3240 cttttctccag atggtgtgcc cggccgggc aggcgcctg gagcctggcg ccccaggcag   3300
ctgctacctg gatgcagggc tgcggcggcg cctgcgggag gagtggggcg tgagctgctg   3360
gaccctgctc caggccccg gagaggccgt gctggtgcct gcaggggctc cccaccaggt   3420
gcagggcctg gtgagcacag tcagcgtcac tcagcacttc ctctcccctg agacctctgc   3480
cctctctgct cagtctctgcc accagggacc cagccttccc cctgactgcc acctgctttta   3540 tgcccagatg gactgggctg tgttccaagc agtgaaggtg gccgtgggga cattacagga   3600
ggccaaatag agggatgcta ggtgtctggg atcggggtgg ggacaggtag accaggtgct   3660
caagcccagg cacaacttca gcagggatg gcgctagggg acttgggat ttctggtca    3719
```

<210> SEQ ID NO 16
<211> LENGTH: 1580
<212> TYPE: PRT
<213> ORGANISM: Homo sapiens

<400> SEQUENCE: 16

```
Met Glu Ala Gln Ser His Ser Ser Thr Thr Thr Glu Lys Lys Lys Val
 1               5                  10                  15

Glu Asn Ser Ile Val Lys Cys Ser Thr Arg Thr Asp Val Ser Glu Lys
             20                  25                  30

Ala Val Ala Ser Ser Thr Thr Ser Asn Glu Asp Glu Ser Pro Gly Gln
         35                  40                  45

Thr Tyr His Arg Glu Arg Arg Asn Ala Ile Thr Met Gln Pro Gln Asn
     50                  55                  60

Val Gln Gly Leu Ser Lys Val Ser Glu Glu Pro Ser Thr Ser Ser Asp
 65                  70                  75                  80

Glu Arg Ala Ser Leu Ile Lys Lys Glu Ile His Gly Ser Leu Pro His
                 85                  90                  95

Val Ala Glu Pro Ser Val Pro Tyr Arg Gly Thr Val Phe Ala Met Asp
            100                 105                 110

Pro Arg Asn Gly Tyr Met Glu Pro His Tyr His Pro Pro His Leu Phe
        115                 120                 125

Pro Ala Phe His Pro Pro Val Pro Ile Asp Ala Arg His His Glu Gly
    130                 135                 140

Arg Tyr His Tyr Asp Pro Ser Pro Ile Pro Pro Leu His Met Thr Ser
145                 150                 155                 160

Ala Leu Ser Ser Ser Pro Thr Tyr Pro Asp Leu Pro Phe Ile Arg Ile
                165                 170                 175

Ser Pro His Arg Asn Pro Ala Ala Ser Glu Ser Pro Phe Ser Pro
            180                 185                 190

Pro His Pro Tyr Ile Asn Pro Tyr Met Asp Tyr Ile Arg Ser Leu His
        195                 200                 205

Ser Ser Pro Ser Leu Ser Met Ile Ser Ala Thr Arg Gly Leu Ser Pro
    210                 215                 220

Thr Asp Ala Pro His Ala Gly Val Ser Pro Ala Glu Tyr Tyr His Gln
225                 230                 235                 240

Met Ala Leu Leu Thr Gly Gln Arg Ser Pro Tyr Ala Asp Ile Ile Pro
                245                 250                 255

Ser Ala Ala Thr Ala Gly Thr Gly Ala Ile His Met Glu Tyr Leu His
            260                 265                 270

Ala Met Asp Ser Thr Arg Phe Ser Ser Pro Arg Leu Ser Ala Arg Pro
        275                 280                 285

Ser Arg Lys Arg Thr Leu Ser Ile Ser Pro Leu Ser Asp His Ser Phe
    290                 295                 300

Asp Leu Gln Thr Met Ile Arg Thr Ser Pro Asn Ser Leu Val Thr Ile
305                 310                 315                 320

Leu Asn Asn Ser Arg Ser Ser Ser Ala Ser Gly Ser Tyr Gly His
                325                 330                 335

Leu Ser Ala Ser Ala Ile Ser Pro Ala Leu Ser Phe Thr Tyr Ser Ser
            340                 345                 350

Ala Pro Val Ser Leu His Met His Gln Gln Ile Leu Ser Arg Gln Gln
        355                 360                 365

Ser Leu Gly Ser Ala Phe Gly His Ser Pro Pro Leu Ile His Pro Ala
```

-continued

```
                370                 375                 380
Pro Thr Phe Pro Thr Gln Arg Pro Ile Pro Gly Ile Pro Thr Val Leu
385                 390                 395                 400

Asn Pro Val Gln Val Ser Ser Gly Pro Ser Glu Ser Ser Gln Asn Lys
                405                 410                 415

Pro Thr Ser Glu Ser Ala Val Ser Ser Thr Gly Asp Pro Met His Asn
            420                 425                 430

Lys Arg Ser Lys Ile Lys Pro Asp Glu Asp Leu Pro Ser Pro Gly Ala
            435                 440                 445

Arg Gly Gln Gln Glu Gln Pro Glu Gly Thr Thr Leu Val Lys Glu Glu
450                 455                 460

Gly Asp Lys Asp Glu Ser Lys Gln Glu Pro Glu Val Ile Tyr Glu Thr
465                 470                 475                 480

Asn Cys His Trp Glu Gly Cys Ala Arg Glu Phe Asp Thr Gln Glu Gln
                485                 490                 495

Leu Val His His Ile Asn Asn Asp His Ile His Gly Glu Lys Lys Glu
            500                 505                 510

Phe Val Cys Arg Trp Leu Asp Cys Ser Arg Glu Gln Lys Pro Phe Lys
            515                 520                 525

Ala Gln Tyr Met Leu Val Val His Met Arg Arg His Thr Gly Glu Lys
            530                 535                 540

Pro His Lys Cys Thr Phe Glu Gly Cys Thr Lys Ala Tyr Ser Arg Leu
545                 550                 555                 560

Glu Asn Leu Lys Thr His Leu Arg Ser His Thr Gly Glu Lys Pro Tyr
                565                 570                 575

Val Cys Glu His Glu Gly Cys Asn Lys Ala Phe Ser Asn Ala Ser Asp
            580                 585                 590

Arg Ala Lys His Gln Asn Arg Thr His Ser Asn Glu Lys Pro Tyr Val
            595                 600                 605

Cys Lys Ile Pro Gly Cys Thr Lys Arg Tyr Thr Asp Pro Ser Ser Leu
            610                 615                 620

Arg Lys His Val Lys Thr Val His Gly Pro Glu Ala His Val Thr Lys
625                 630                 635                 640

Lys Gln Arg Gly Asp Ile His Pro Arg Pro Pro Pro Arg Asp Ser
                645                 650                 655

Gly Ser His Ser Gln Ser Arg Ser Pro Gly Arg Pro Thr Gln Gly Ala
                660                 665                 670

Leu Gly Glu Gln Gln Asp Leu Ser Asn Thr Thr Ser Lys Arg Glu Glu
            675                 680                 685

Cys Leu Gln Val Lys Thr Val Lys Ala Glu Lys Pro Met Thr Ser Gln
690                 695                 700

Pro Ser Pro Gly Gly Gln Ser Ser Cys Ser Ser Gln Ser Pro Ile
705                 710                 715                 720

Ser Asn Tyr Ser Asn Ser Gly Leu Glu Leu Pro Leu Thr Asp Gly Gly
                725                 730                 735

Ser Ile Gly Asp Leu Ser Ala Ile Asp Glu Thr Pro Ile Met Asp Ser
            740                 745                 750

Thr Ile Ser Thr Ala Thr Thr Ala Leu Ala Leu Gln Ala Arg Arg Asn
            755                 760                 765

Pro Ala Gly Thr Lys Trp Met Glu His Val Lys Leu Glu Arg Leu Lys
770                 775                 780

Gln Val Asn Gly Met Phe Pro Arg Leu Asn Pro Ile Leu Pro Pro Lys
785                 790                 795                 800
```

-continued

```
Ala Pro Ala Val Ser Pro Leu Ile Gly Asn Gly Thr Gln Ser Asn Asn
                805                 810                 815
Thr Cys Ser Leu Gly Gly Pro Met Thr Leu Leu Pro Gly Arg Ser Asp
            820                 825                 830
Leu Ser Gly Val Asp Val Thr Met Leu Asn Met Leu Asn Arg Arg Asp
        835                 840                 845
Ser Ser Ala Ser Thr Ile Ser Ser Ala Tyr Leu Ser Ser Arg Arg Ser
    850                 855                 860
Ser Gly Ile Ser Pro Cys Phe Ser Ser Arg Arg Ser Ser Glu Ala Ser
865                 870                 875                 880
Gln Ala Glu Gly Arg Pro Gln Asn Val Ser Val Ala Asp Ser Tyr Asp
                885                 890                 895
Pro Ile Ser Thr Asp Ala Ser Arg Arg Ser Ser Glu Ala Ser Gln Ser
            900                 905                 910
Asp Gly Leu Pro Ser Leu Leu Ser Leu Thr Pro Ala Gln Gln Tyr Arg
        915                 920                 925
Leu Lys Ala Lys Tyr Ala Ala Ala Thr Gly Gly Pro Pro Thr Pro
    930                 935                 940
Leu Pro Asn Met Glu Arg Met Ser Leu Lys Thr Arg Leu Ala Leu Leu
945                 950                 955                 960
Gly Asp Ala Leu Glu Pro Gly Val Ala Leu Pro Pro Val His Ala Pro
                965                 970                 975
Arg Arg Cys Ser Asp Gly Gly Ala His Gly Tyr Gly Arg Arg His Leu
            980                 985                 990
Gln Pro His Asp Ala Leu Gly His Gly Val Arg Arg Ala Ser Asp Pro
        995                 1000                1005
Val Arg Thr Gly Ser Glu Gly Leu Ala Leu Pro Arg Val Pro Arg Phe
    1010                1015                1020
Ser Ser Leu Ser Ser Cys Asn Pro Pro Ala Met Ala Thr Ser Ala Glu
1025                1030                1035                1040
Lys Arg Ser Leu Val Leu Gln Asn Tyr Thr Arg Pro Glu Gly Gly Gln
                1045                1050                1055
Ser Arg Asn Phe His Ser Ser Pro Cys Pro Pro Ser Ile Thr Glu Asn
            1060                1065                1070
Val Thr Leu Glu Ser Leu Thr Met Asp Ala Asp Ala Asn Leu Asn Asp
        1075                1080                1085
Glu Asp Phe Leu Pro Asp Asp Val Val Gln Tyr Leu Asn Ser Gln Asn
    1090                1095                1100
Gln Ala Gly Tyr Glu Gln His Phe Pro Ser Ala Leu Pro Asp Asp Ser
1105                1110                1115                1120
Lys Val Pro His Gly Pro Gly Asp Phe Asp Ala Pro Gly Leu Pro Asp
                1125                1130                1135
Ser His Ala Gly Gln Gln Phe His Ala Leu Glu Gln Pro Cys Pro Glu
            1140                1145                1150
Gly Ser Lys Thr Asp Leu Pro Ile Gln Trp Asn Glu Val Ser Ser Gly
        1155                1160                1165
Ser Ala Asp Leu Ser Ser Ser Lys Leu Lys Cys Gly Pro Arg Pro Ala
    1170                1175                1180
Val Pro Gln Thr Arg Ala Phe Gly Phe Cys Asn Gly Met Val Val His
1185                1190                1195                1200
Pro Gln Asn Pro Leu Arg Ser Gly Pro Ala Gly Gly Tyr Gln Thr Leu
                1205                1210                1215
```

-continued

Gly Glu Asn Ser Asn Pro Tyr Gly Gly Pro Glu His Leu Met Leu His
         1220                1225                1230

Asn Ser Pro Gly Ser Gly Thr Ser Gly Asn Ala Phe His Glu Gln Pro
         1235                1240                1245

Cys Lys Ala Pro Gln Tyr Gly Asn Cys Leu Asn Arg Gln Pro Val Ala
1250                1255                1260

Pro Gly Ala Leu Asp Gly Ala Cys Gly Ala Gly Ile Gln Ala Ser Lys
1265                1270                1275                1280

Leu Lys Ser Thr Pro Met Gln Gly Ser Gly Gln Leu Asn Phe Gly
         1285                1290                1295

Leu Pro Val Ala Pro Asn Glu Ser Ala Gly Ser Met Val Asn Gly Met
         1300                1305                1310

Gln Asn Gln Asp Pro Val Gly Gln Gly Tyr Leu Ala His Gln Leu Leu
         1315                1320                1325

Gly Asp Ser Met Gln His Pro Gly Ala Gly Arg Pro Gly Gln Gln Met
         1330                1335                1340

Leu Gly Gln Ile Ser Ala Thr Ser His Ile Asn Ile Tyr Gln Gly Pro
1345                1350                1355                1360

Glu Ser Cys Leu Pro Gly Ala His Gly Met Gly Ser Gln Pro Ser Ser
         1365                1370                1375

Leu Ala Val Val Arg Gly Tyr Gln Pro Cys Ala Ser Phe Gly Gly Ser
         1380                1385                1390

Arg Arg Gln Ala Met Pro Arg Asp Ser Leu Ala Leu Gln Ser Gly Gln
         1395                1400                1405

Leu Ser Asp Thr Ser Gln Thr Cys Arg Val Asn Gly Ile Lys Met Glu
         1410                1415                1420

Met Lys Gly Gln Pro His Pro Leu Cys Ser Asn Leu Gln Asn Tyr Ser
1425                1430                1435                1440

Gly Gln Phe Tyr Asp Gln Thr Val Gly Phe Ser Gln Gln Asp Thr Lys
         1445                1450                1455

Ala Gly Ser Phe Ser Ile Ser Asp Ala Ser Cys Leu Leu Gln Gly Thr
         1460                1465                1470

Ser Ala Lys Asn Ser Glu Leu Leu Ser Pro Gly Ala Asn Gln Val Thr
         1475                1480                1485

Ser Thr Val Asp Ser Leu Asp Ser His Asp Leu Glu Gly Val Gln Ile
         1490                1495                1500

Asp Phe Asp Ala Ile Ile Asp Asp Gly Asp His Ser Ser Leu Met Ser
1505                1510                1515                1520

Gly Ala Leu Ser Pro Ser Ile Ile Gln Asn Leu Ser His Ser Ser Ser
         1525                1530                1535

Arg Leu Thr Thr Pro Arg Ala Ser Leu Pro Phe Pro Ala Leu Ser Met
         1540                1545                1550

Ser Thr Thr Asn Met Ala Ile Gly Asp Met Ser Ser Leu Leu Thr Ser
         1555                1560                1565

Leu Ala Glu Glu Ser Lys Phe Leu Ala Val Met Gln
      1570                1575                1580

<210> SEQ ID NO 17
<211> LENGTH: 5054
<212> TYPE: DNA
<213> ORGANISM: Homo sapiens

<400> SEQUENCE: 17
cgatactacg tgggcatttt tggtcgaaga gagctgaagt aatgagaaga catcatggag    60

```
gcccagtccc acagctccac gaccactgaa agaaaaaag ttgagaattc catagtgaag    120
tgctccactc gaacagatgt gagcgagaaa gccgttgcct ccagcaccac ttctaatgag    180
gatgaaagtc ctggacagac ttatcacaga gagagaagaa acgcaatcac tatgcagcca    240
cagaatgtcc aggggctcag caaagtcagt gaggaacctt caacatcgag tgacgagagg    300
gcctcattga tcaagaaaga gatccatggg tccctgccac acgtggcgga gccctctgtg    360
ccgtaccgcg ggacggtgtt tgccatggac cccaggaatg gttacatgga gccccactac    420
caccctcctc atcttttccc tgccttccat cctcctgtac caattgatgc cagacatcat    480
gagggccgtt accattacga tccatctccg attcctccat gcatatgact tccgcctta    540 tctagtagcc ctacgtatcc ggacctgccc ttcattagga tctccccaca ccggaacccc    600
gctgctgctt ccgagtctcc cttcagccct ccacatccct acattaatcc ctacatggac    660
tatatccgct ccttgcacag cagcccatcg ctctccatga tctcagcaac ccgtgggctg    720
agccctacag atgcgcccca tgcaggagtc agcccagcag aatactatca tcagatggcc    780
ctgctaactg gccagcgcag cccctatgca gacattattc cctcagctgc caccgccggc    840
acgggggcca tccacatgga atatcttcat gctatggata gcaccagatt ctccagcccc    900
aggctgtcag ccaggccgag ccgaaaacgt acactgtcca tatcaccact ctccgatcat    960
agctttgacc ttcagaccat gataaggacg tctcccaact ccttggtcac gattctcaat   1020
aattcccgta gcagctcttc agcaagtggc tcctatggtc acttatctgc aagtgcaatc   1080
agccctgcct tgagcttcac ctactcttcc gcgcccgtct ctctccacat gcatcagcag   1140
atcctaagcc gacaacagag cttaggttca gcctttggac acagccctcc actcatccac   1200
cctgccccaa cttttccaac acagaggcct attccaggga tccctacggt tctgaacccc   1260
gtccaggtca gctccggccc ttctgagtcc tcacagaaca agcccacgag tgagtctgca   1320
gtgagcagca ctggtgaccc gatgcacaac aagaggtcca agatcaaacc cgatgaagac   1380
ctccccagcc caggggctcg ggggcagcag aacagcccg aaggaacaac ccttgtcaag   1440
gaggaagggg acaaagatga agcaaacag gagcctgaag tcatctatga dacaaactgc   1500
cactgggaag gctgcgcgag ggagttcgac acccaagagc agcttgtgca ccatataaat   1560
aacgaccata ttcatggaga gaagaaggag ttcgtgtgca ggtggctgga ctgctcaaga   1620
gagcagaaac ccttcaaagc ccagtatatg ttggtagtgc atatgagaag acacacgggc   1680
gagaagcctc acaaatgcac ttttgaaggt tgcacaaagg cctactcgag actagaaaac   1740
ttgaaaacac acttgagatc tcacactgga gagaaaccat acgtctgtga gcacgaaggt   1800
tgcaacaagg ctttctcaaa tgcctctgat cgcgccaaac accaaaacag aacgcattcc   1860
aatgagaaac catatgtgtg caaaatccca ggctgcacta agcgttacac agacccaagc   1920
tccctccgga aacatgtgaa gacagtgcat ggcccagagg ctcatgtcac caagaagcag   1980 cgagggaca tccatcctcg gccgccaccc ccgagagatt ccggcagcca ttcacagtcc   2040
aggtcgcctg gccgaccgac tcagggagcc cttggtgagc agcaggacct cagcaacact   2100
acctcaaagc gggaagaatg cctccaggtg aaaaccgtca aggcagagaa gccaatgaca   2160
tctcagccaa gcctggtgg tcagtcttca tgcagcagcc aacagtcccc catcagcaac   2220
tattccaaca gtgggctcga gcttcctctg accgatggag gtagtatagg agacctcagt   2280
gccatcgatg aaaccccaat catggactca accatttcca ctgcaaccac agcccttgct   2340
ttgcaagcca ggagaaaccc ggcagggacc aaatggatgg agcacgtaaa actagaaagg   2400
ctaaaacaag tgaatggaat gtttccgcga ctgaacccca ttctaccccc taaagcccct   2460
```

-continued

```
gcggtctctc ctctcatagg aaatggcaca cagtccaaca acacctgcag cttgggtggg    2520
cccatgacgc ttctcccggg cagaagcgac ctctctgggg tggacgtcac tatgctgaac    2580
atgctcaaca gaagggacag cagcgccagc accatcagct cggcctacct gagcagccgc    2640
cgctcctcag ggatctcgcc ctgcttctcc agccgccgct ccagcgaggc gtcacaggcc    2700
gagggccggc cgcagaacgt gagcgtggcc gactcctacg accccatctc caccgacgcc    2760
tcgcgccgct ccagcgaagc cagccagagc gacggcctgc ccagcctgct cagcctcacg    2820
cccgcccagc agtaccgcct caaggccaag tacgcggctg ccacaggagg gccgccgccg    2880
acgcccctgc ccaacatgga gaggatgagc ctgaagacgc gcctggcgct gctcggggat    2940
gccctcgagc ctggcgtggc cctgcctcca gttcatgccc cgaggaggtg cagcgacggg    3000
ggagcccacg gctacgggcg cgccacctg cagccgcacg atgcgctggg ccacggcgtg    3060
aggagggcca cgaccccggt gcggacaggc tccagggcc tggccctgcc tcgtgtgccg    3120
cgcttcagca gcctcagcag ctgcaaccc ccggcgatgg ccacgtccgc ggagaagcgc    3180
agtctcgtgc ttcagaatta cacgcggccc gagggcggcc agtcccgaaa cttccactcg    3240
tccccctgtc ctcccagcat caccgagaac gtcaccctgg agtccctgac catggacgct    3300
gatgccaacc tgaacgatga ggatttcctg ccggacgacg tggtgcagta tttaaattcc    3360
cagaaccaag cagggtacga gcagcacttc cccagcgccc tccgacga cagcaaagtg    3420 ccccacgggc ccggtgactt tgacgcgccc gggctgccag acagccacgc tggccagcag    3480
ttccatgccc tcgagcagcc ctgccccgag ggcagcaaaa ccgacctgcc cattcagtgg    3540
aacgaagtca gctccggaag cgccgacctg tcctcctcca agctcaagtg tgggccgcgg    3600
cccgctgtgc cgcagactcg cgcctttggg ttctgcaacg gcatggtcgt ccacccgcag    3660
aaccccttga ggagcgggcc tgctgggggc tatcagaccc tcgggagaa cagcaacccc    3720 tacggtggcc cagagcactt gatgctccac aacagccccg gaagtggcac cagtggaaac    3780
gccttccatg aacagccctg taaggccccg cagtatggga actgtctcaa caggcagcca    3840
gtggcccctg gtgcactcga cggtgcctgt ggtgccggga ttcaagcctc aaagctgaag    3900 agcacccca tgcaagggag cgggggccag ctgaatttcg gcctgccggt agcgccaaat    3960
gagtcagctg gcagcatggt gaatggcatg cagaaccagg acccagtggg acaggggtac    4020
ctggctcacc agctcctcgg cgacagcatg cagcacccgg gggcaggccg ccccggtcag    4080
cagatgcttg gcagattag tgctacctca cacatcaaca tctaccaagg ccagagagc    4140 tgcctgccag gggctcacgg catgggcagc cagccgtcaa gcttggcagt tgtcaggggc    4200
taccagccat gtgccagctt tggggcagc aggcgccagg ctatgccgag ggacagcctt    4260
gctctgcagt caggacagct cagtgacaca agtcagacct gcaggtgaa tggtatcaag    4320 atggagatga aagggcagcc ccatccgctg tgctctaatc tgcagaatta ctctggtcag    4380
ttctatgacc aaaccgtggg cttcagtcag caagacacga aagctggttc attctctatt    4440
tcagacgcca gctgcctgct acaggggacc agcgccaaaa actctgagtt actttccccca    4500 ggtgctaatc aggtgacaag cacagtggac agcctcgaca gccatgacct ggaaggggta    4560
cagattgact tcgatgccat catagacgat ggggaccact ccagcctgat gtcgggggcc    4620
ctgagcccaa gtatcattca gaacctttcc catagctcct cccgcctcac cacgcctcgg    4680
gcgtccctcc cattcccagc gctgtccatg agcaccacca acatggctat cggggacatg    4740
agttctttgc tgacctccct agcggaagaa agcaaattcc ttgcagttat gcaataggct    4800
```

-continued ttaggaaaaa aagactgcaa ccaacggaaa tcaataggag ttgaagagat taaactgact    4860
ttgttttggc tgttttttta gttctgtatg tattttagca atctcatctc acctaactga    4920
gatgtgtttc aattatattc cttttatgga aaaggactct gaaaaaccct aaagtattct    4980
agggagaaac tgtcttccat ttcagttttg aatcagtatt gttacactca aaccaccctc    5040
tttttaaaaa aaaa    5054

<210> SEQ ID NO 18
<211> LENGTH: 732
<212> TYPE: PRT
<213> ORGANISM: Homo sapiens

<400> SEQUENCE: 18

Met Pro Glu Glu Thr Gln Thr Gln Asp Gln Pro Met Glu Glu Glu
 1               5                  10                  15

Val Glu Thr Phe Ala Phe Gln Ala Glu Ile Ala Gln Leu Met Ser Leu
                20                  25                  30

Ile Ile Asn Thr Phe Tyr Ser Asn Lys Glu Ile Phe Leu Arg Glu Leu
            35                  40                  45

Ile Ser Asn Ser Ser Asp Ala Leu Asp Lys Ile Arg Tyr Glu Thr Leu
        50                  55                  60

Thr Asp Pro Ser Lys Leu Asp Ser Gly Lys Glu Leu His Ile Asn Leu
65                  70                  75                  80

Ile Pro Asn Lys Gln Asp Arg Thr Leu Thr Ile Val Asp Thr Gly Ile
                85                  90                  95

Gly Met Thr Lys Ala Asp Leu Ile Asn Asn Leu Gly Thr Ile Ala Lys
            100                 105                 110

Ser Gly Thr Lys Ala Phe Met Glu Ala Leu Gln Ala Gly Ala Asp Ile
        115                 120                 125

Ser Met Ile Gly Gln Phe Gly Val Gly Phe Tyr Ser Ala Tyr Leu Val
    130                 135                 140

Ala Glu Lys Val Thr Val Ile Thr Lys His Asn Asp Asp Glu Gln Tyr
145                 150                 155                 160

Ala Trp Glu Ser Ser Ala Gly Gly Ser Phe Thr Val Arg Thr Asp Thr
                165                 170                 175

Gly Glu Pro Met Gly Arg Gly Thr Lys Val Ile Leu His Leu Lys Glu
            180                 185                 190

Asp Gln Thr Glu Tyr Leu Glu Glu Arg Arg Ile Lys Glu Ile Val Lys
        195                 200                 205

Lys His Ser Gln Phe Ile Gly Tyr Pro Ile Thr Leu Phe Val Glu Lys
    210                 215                 220

Glu Arg Asp Lys Glu Val Ser Asp Asp Glu Ala Glu Glu Lys Glu Asp
225                 230                 235                 240

Lys Glu Glu Glu Lys Glu Lys Glu Glu Lys Glu Ser Glu Asp Lys Pro
                245                 250                 255

Glu Ile Glu Asp Val Gly Ser Asp Glu Glu Glu Glu Lys Lys Asp Gly
            260                 265                 270

Asp Lys Lys Lys Lys Lys Ile Lys Glu Lys Tyr Ile Asp Gln Glu
        275                 280                 285

Glu Leu Asn Lys Thr Lys Pro Ile Trp Thr Arg Asn Pro Asp Asp Ile
    290                 295                 300

Thr Asn Glu Glu Tyr Gly Glu Phe Tyr Lys Ser Leu Thr Asn Asp Trp
305                 310                 315                 320

Glu Asp His Leu Ala Val Lys His Phe Ser Val Glu Gly Gln Leu Glu

-continued

```
                325                 330                 335
Phe Arg Ala Leu Leu Phe Val Pro Arg Arg Ala Pro Phe Asp Leu Phe
            340                 345                 350
Glu Asn Arg Lys Lys Lys Asn Asn Ile Lys Leu Tyr Val Arg Arg Val
        355                 360                 365
Phe Ile Met Asp Asn Cys Glu Glu Leu Ile Pro Glu Tyr Leu Asn Phe
    370                 375                 380
Ile Arg Gly Val Val Asp Ser Glu Asp Leu Pro Leu Asn Ile Ser Arg
385                 390                 395                 400
Glu Met Leu Gln Gln Ser Lys Ile Leu Lys Val Ile Arg Lys Asn Leu
            405                 410                 415
Val Lys Lys Cys Leu Glu Leu Phe Thr Glu Leu Ala Glu Asp Lys Glu
        420                 425                 430
Asn Tyr Lys Lys Phe Tyr Glu Gln Phe Ser Lys Asn Ile Lys Leu Gly
    435                 440                 445
Ile His Glu Asp Ser Gln Asn Arg Lys Lys Leu Ser Glu Leu Leu Arg
    450                 455                 460
Tyr Tyr Thr Ser Ala Ser Gly Asp Glu Met Val Ser Leu Lys Asp Tyr
465                 470                 475                 480
Cys Thr Arg Met Lys Glu Asn Gln Lys His Ile Tyr Tyr Ile Thr Gly
            485                 490                 495
Glu Thr Lys Asp Gln Val Ala Asn Ser Ala Phe Val Glu Arg Leu Arg
        500                 505                 510
Lys His Gly Leu Glu Val Ile Tyr Met Ile Glu Pro Ile Asp Glu Tyr
    515                 520                 525
Cys Val Gln Gln Leu Lys Glu Phe Glu Gly Lys Thr Leu Val Ser Val
    530                 535                 540
Thr Lys Glu Gly Leu Glu Leu Pro Glu Asp Glu Glu Lys Lys Lys
545                 550                 555                 560
Gln Glu Glu Lys Lys Thr Lys Phe Glu Asn Leu Cys Lys Ile Met Lys
            565                 570                 575
Asp Ile Leu Glu Lys Lys Val Glu Lys Val Val Ser Asn Arg Leu
        580                 585                 590
Val Thr Ser Pro Cys Cys Ile Val Thr Ser Thr Tyr Gly Trp Thr Ala
    595                 600                 605
Asn Met Glu Arg Ile Met Lys Ala Gln Ala Leu Arg Asp Asn Ser Thr
    610                 615                 620
Met Gly Tyr Met Ala Ala Lys Lys His Leu Glu Ile Asn Pro Asp His
625                 630                 635                 640
Ser Ile Ile Glu Thr Leu Arg Gln Lys Ala Glu Ala Asp Lys Asn Asp
            645                 650                 655
Lys Ser Val Lys Asp Leu Val Ile Leu Leu Tyr Glu Thr Ala Leu Leu
        660                 665                 670
Ser Ser Gly Phe Ser Leu Glu Asp Pro Gln Thr His Ala Asn Arg Ile
    675                 680                 685
Tyr Arg Met Ile Lys Leu Gly Leu Gly Ile Asp Glu Asp Pro Thr
    690                 695                 700
Ala Asp Asp Thr Ser Ala Ala Val Thr Glu Glu Met Pro Pro Leu Glu
705                 710                 715                 720
Gly Asp Asp Asp Thr Ser Arg Met Glu Glu Val Asp
            725                 730
```

<210> SEQ ID NO 19

<211> LENGTH: 2259
<212> TYPE: DNA
<213> ORGANISM: Homo sapiens

<400> SEQUENCE: 19

```
cagttgcttc agcgtcccgg tgtggctgtg ccgttggtcc tgtgcggtca cttagccaag      60
atgcctgagg aaacccagac ccaagaccaa ccgatggagg aggaggaggt tgagacgttc     120
gcctttcagg cagaaattgc ccagttgatg tcattgatca tcaatacttt ctactcgaac     180
aaagagatct ttctgagaga gctcatttca aattcatcag atgcattgga caaaatccgg     240
tatgaaactt tgacagatcc cagtaaatta gactctggga agagctgca tattaacctt      300
ataccgaaca aacaagatcg aactctcact attgtggata ctggaattgg aatgaccaag     360
gctgacttga tcaataacct tggtactatc gccaagtctg ggaccaaagc gttcatggaa     420
gctttgcagg ctggtgcaga tatctctatg attggccagt tcggtgttgg ttttattct      480
gcttatttgg ttgctgagaa agtaactgtg atcaccaaac ataacgatga tgagcagtac     540
gcttgggagt cctcagcagg gggatcattc acagtgagga cagacacagg tgaacctatg     600
ggtcgtggaa caaagttat cctacacctg aagaagacc aaactgagta cttggaggaa       660
cgaagaataa aggagattgt gaagaaacat tctcagttta ttggatatcc cattactctt     720
tttgtggaga aggaacgtga taagaagta agcgatgatg aggctgaaga aaaggaagac     780
aaagaagaag aaaaagaaaa agaagagaaa gagtcggaag acaaacctga aattgaagat     840
gttggttctg atgaggaaga agaaaagaag gatggtgaca agaagaagaa gaagaagatt    900
aaggaaaagt acatcgatca agaagagctc aacaaaacaa agcccatctg gaccagaaat     960
cccgacgata ttactaatga ggagtacgga gaattctata agagcttgac caatgactgg    1020
gaagatcact tggcagtgaa gcatttttca gttgaaggac agttggaatt cagagccctt    1080
ctatttgtcc cacgacgtgc tccttttgat ctgtttgaaa acagaaagaa aaagaacaat    1140
atcaaattgt atgtacgcag agttttcatc atggataact gtgaggagct aatccctgaa    1200
tatctgaact tcattagagg ggtggtagac tcggaggatc tccctctaaa catatcccgt    1260
gagatgttgc aacaaagcaa aattttgaaa gttatcagga gaatttggt caaaaaatgc    1320
ttagaactct ttactgaact ggcggaagat aaagagaact acaagaaatt ctatgagcag    1380
ttctctaaaa acataaagct tggaatacac gaagactctc aaaatcggaa gaagctttca    1440
gagctgttaa ggtactacac atctgcctct ggtgatgaga tggtttctct caaggactac    1500
tgcaccagaa tgaaggagaa ccagaaacat atctattata tcacaggtga gaccaaggac    1560
caggtagcta actcagcctt tgtggaacgt cttcggaaac atggcttaga agtgatctat    1620
atgattgagc ccattgatga gtactgtgtc aacagctga aggaatttga ggggaagact    1680
ttagtgtcag tcaccaaaga aggcctggaa cttccagagg atgaagaaga gaaaagaag    1740
caggaagaga aaaaacaaa gtttgagaac ctctgcaaaa tcatgaaaga catattggag    1800
aaaaaagttg aaaaggtggt tgtgtcaaac cgattggtga catctccatg ctgtattgtc    1860
acaagcacat atggctggac agcaaacatg gagagaatca tgaaagctca gcccctaaga    1920
gacaactcaa caatgggtta catggcagca agaaacacc tggagataaa ccctgaccat    1980
tccattattg agaccttaag gcaaaaggca gaggctgata gaacgacaa gtctgtgaag    2040
gatctggtca tcttgctta tgaaactgcg ctcctgtctt ctggcttcag tctggaagat    2100
ccccagacac atgctaacag gatctacagg atgatcaaac ttggtctggg tattgatgaa    2160
gatgacccta ctgctgatga taccagtgct gctgtaactg aagaaatgcc accccttgaa    2220
```

```
ggagatgacg acacatcacg catggaagaa gtagactaa                          2259

<210> SEQ ID NO 20
<211> LENGTH: 108
<212> TYPE: PRT
<213> ORGANISM: Homo sapiens

<400> SEQUENCE: 20

Pro Gln Leu Lys Pro Pro Arg Arg Asn His Leu Cys Cys Gln Ser Pro
 1               5                  10                  15

Glu Gly Ala Thr Gln Arg Ala Leu Leu Ala Leu Cys Gln Val Val Lys
            20                  25                  30

Ala Ala Pro Cys Phe Leu Lys Arg Glu Glu Ala Ile Phe Gly Pro Pro
        35                  40                  45

Phe Val Thr Ser Ser Leu Asn Ala Ser Ser Phe Arg Thr Gly Phe Ser
    50                  55                  60

Pro Phe Arg Gln Val Arg Phe Leu Arg Arg Asn Pro Val Ser Lys Ile
65                  70                  75                  80

Phe Lys Gly Val Ser Leu Gln Pro Leu Ile Ser Leu Val Leu Met Val
                85                  90                  95

Phe Asn Phe Pro Phe Leu Phe Leu Gly Phe Gly Phe
            100                 105

<210> SEQ ID NO 21
<211> LENGTH: 326
<212> TYPE: DNA
<213> ORGANISM: Homo sapiens

<400> SEQUENCE: 21
ccgcagttaa agcccccaag aagaaaccat ctgtgctgcc agtcacccga aggtgccact     60
caacgagccc tgttggcact ttgccaagtg gttaaggcag ccccttgttt tttgaaacgt    120
gaagaagcga tatttggacc acctttcgtc acgagcagtt taaatgccag cagttttaga    180
accgggtttt cccctttag gcaagttagg ttcttgcgga ggaatccagt tagtaagatt     240
tttaaggggg tttccctcca acccttaatt agtttggttt taatggtatt taactttcca    300
ttcctgtttt tggggtttgg tttttt                                        326
```